US008574598B2

(12) United States Patent
Lemesre et al.

(10) Patent No.: US 8,574,598 B2
(45) Date of Patent: Nov. 5, 2013

(54) AGENTS FOR THE PREVENTION OF LEISHMANIASIS

(75) Inventors: Jean-Loup Lemesre, Montpellier (FR); Mireille Cavaleyra, Montpellier (FR); Denis Sereno, Poussan (FR); Philippe Holzmuller, Montpellier (FR)

(73) Assignee: Institut de Recherche Pour le Developpement (IRD), Paris Cedex (FR)

( * ) Notice: Subject to any disclaimer, the term of this patent is extended or adjusted under 35 U.S.C. 154(b) by 805 days.

(21) Appl. No.: 10/579,749

(22) PCT Filed: Nov. 19, 2004

(86) PCT No.: PCT/FR2004/002955
§ 371 (c)(1),
(2), (4) Date: Feb. 16, 2007

(87) PCT Pub. No.: WO2005/051989
PCT Pub. Date: Jun. 9, 2005

(65) Prior Publication Data
US 2008/0026467 A1 Jan. 31, 2008

(30) Foreign Application Priority Data

Nov. 19, 2003 (FR) .................................... 03 13555
Jun. 25, 2004 (FR) .................................... 04 07010

(51) Int. Cl.
*A61K 39/002* (2006.01)
(52) U.S. Cl.
USPC ....................... 424/269.1; 424/191.1; 530/350
(58) Field of Classification Search
None
See application file for complete search history.

(56) References Cited

U.S. PATENT DOCUMENTS

| 2002/0169285 | A1* | 11/2002 | Reed et al. ..................... 530/350 |
| 2003/0068690 | A1* | 4/2003 | Lemesre ........................ 435/69.1 |
| 2003/0157125 | A1* | 8/2003 | Alvarez et al. ............. 424/191.1 |
| 2008/0026467 | A1  | 1/2008 | Lemesre et al. |
| 2009/0214595 | A1  | 8/2009 | Lemesre et al. |

FOREIGN PATENT DOCUMENTS

WO  94/26899  11/1994

OTHER PUBLICATIONS

Breitlow (Promega Notes Magazine No. 35, Feb. 1992).*
International Search Report for PCT/FR04/02955 dated Aug. 17, 2005.
Loman et al., *Molecular cloning and characterization of the immunologically protective surface glycoprotein GP46/M-2 of Leishmania amazonensis*, Proceedings of the National Academy of Sciences of USA, vol. 87, Nov. 1990, pp. 8393-8397, XP002204079.
Dumonteil et al., *DNA vaccines induce partial protection against Leishmania mexicana*, Vaccine, vol. 21, No. 17-18, May 16, 2003, pp. 2170-2177, XP004421134.
Handman et al., *Therapy of murine cutaneous leishmaniasis by DNA vaccination*, Vaccine, vol. 18, No. 26, Jul. 2000, pp. 3011-3017, XP004199096.
Lebowitz et al., *Development of a Stable Leishmania Expression Vector and Application to the Study of Parasite Surface Antigen Genes*, Proceedings of the National Academy of Science, vol. 87, Dec. 1990, pp. 9736-9740, XP002052133.
Kima et al., *Presentation via the class I pathway by Leishmania amazonensis-infected macrophages of an endogenous leishmanial antigen to CD8+ T cells*, Journal of Immunology, Aug. 15, 1997, vol. 159, No. 4, pp. 1828-1834, XP002336360.
Jimenez-Ruiz et al., *Cloning Sequencing and Expression of the PSA Genes from Leishmania Infantum*, European Journal of Biochemistry, vol. 251, No. 1 / 2, Jan. 15, 1998, pp. 389-397, XP001159173.
Murray et al., *Variants of a Leishmania Surface Antigen Derived from a Multigenic Family*, Journal of Biological Chemistry, vol. 266, No. 36, 1991, pp. 24477-24484, XP002296789.
Symons et al., *Characterization of a polymorphic family of integral membrane proteins in promastigotes of different Leishmania species*, Molecular and Biochemical Parasitology, vol. 67, No. 1, 1994, pp. 103-113, XP002336361.
Beetham et al., *Glycoprotein 46 mRNA abundance is post-transcriptionally regulated during development of Leishmania chagasi promastigotes to an infectious form*, Journal of Biological Chemistry, vol. 272, No. 28, 1997, pp. 17360-17366, XP002296788.
International Search Report for PCT/FR2006/000314 mailed Jun. 21, 2006 (English and French).
Chen et al., "Episomal Expression of Specific Sense and Antisense MRNAs in *Leishmania amazonensis*: Modulation of GP63 Level in Promatigotes and their Infection of Macrophages In Vitro," Infection and Immunity, vol. 68, No. 1, 2000, 1980 p. 86.
Hajmova et al., "Down Regulation of GP63 in *Leishmania amazonensis* Reduces its Early Development in *Lutzomyia longialpis*," Microbes and Infection, vol. 6, 2004, pp. 646-649.
Joshi et al., "Targeted Gene Deletion in *Leishmania* Major Identifies Leishmanolysin (GP63) as a Virulence Factor," Molecular and Biochemical Parasitology, vol. 120, 2002, pp. 33-40.
Beverley et al., "Flypaper for Parasites," Cell, vol. 119, Oct. 29, 2004, pp. 311-316.
Office Action mailed Mar. 24, 2010, issued in copending U.S. Appl. No. 11/884,015.
Pending claims filed Jul. 26, 2010, in copending U.S. Appl. No. 11/884,015.

* cited by examiner

*Primary Examiner* — Patricia A Duffy
(74) *Attorney, Agent, or Firm* — Nixon & Vanderhye P.C.

(57) ABSTRACT

The invention relates to nucleic acid constructions, characterized in that they comprise nucleic acids which are isolated in the sense position and which are capable of coding for an immunogenic protein of promastigotes or amastigotes of *Leishmania*, said nucleic acids responding to one of the sequences SEQ ID No. 1, SEQ ID No. 2, SEQ ID No. 3, SEQ ID No. 4, SEQ ID No. 5 et SEQ ID No. 11 and coding for a protein respectively exhibiting a sequence SEQ ID No. 6, SEQ ID No. 7, SEQ ID No. 8, SEQ ID No. 9, SEQ ID No. 10 et SEQ ID No. 12. The invention can be used for over-expression of the genes of *Leishmania* coding for an excretion/secretion antigen.

10 Claims, 14 Drawing Sheets

FIGURE 1

Figure 2:
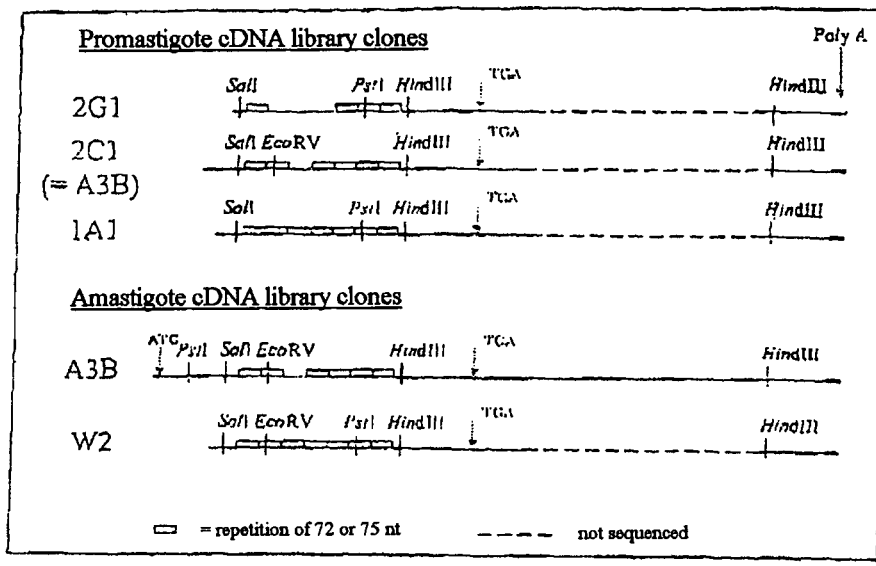

Alignment of the various cDNA sequences obtained

FIGURE 1 (continued)

3' Alignment of the nucleotide sequences of the various cDNA clones

| SEQ ID N°1 | A3B |
| SEQ ID N°2 | 2C1 |
| SEQ ID N°3 | 1A1 |
| SEQ ID N°4 | 2G1 |
| SEQ ID N°5 | W2 |

- Constitutive proteins
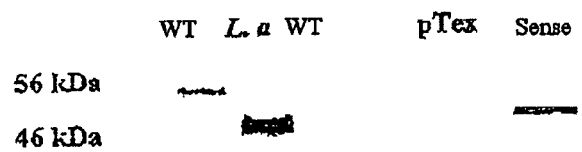
- Excreted/secreted proteins (200 times concentrated culture supernatant)
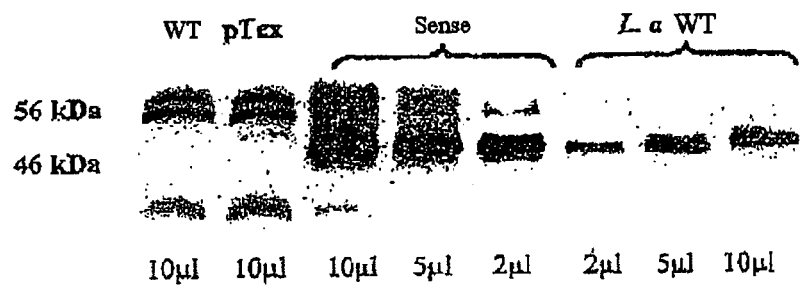
FIGURE 5

PI = Parasitic Index. The variation in PI makes it possible to evaluate the infectious capacity of the Sense strain of interest, as a function of the percentage of infected macrophages and of the number of parasites per macrophage, relative to a control strain pTex.

SEQ ID No 1 (Nucleic sequence A3B)

```
GACCCCTGTTGCGAATGGCCCAGTCCGTCCGTCGGCTGGTGCTGGCGGCGCCCTCGCCCTGTGG
TGGCGCTGCTGCTGTGCACGAGCAGTGCACCGGTGGCGCGTGCTGCGGGGACGAGCGACTTCACTG
AGGCGCAGCAGACGAACACGCTGACGGTGCTGCAGGCGTTTGCGCGTGCGATCGCTGCGCTTGGG
GACACGTGGACGGGCAGCGACTTCTGCTCGTGGAAGCACATCATCTGGGACTCGCCCCGGCGTCGGC
GTGTGGATGGGCGATGTGGATTATACCGGCACGCTGCCGGAGATGCCTGCGAGCGTCGACTACAA
GGACGTCATGATCACGGAACTGAACTTCAGCGCAATGGGCCAGGGGCTGAGCGGGACGCTGCCCC
CCTCATGGAGCTCGCTGACGTCCTTGATATCACTGTGCATCGAAAAGTCTGAGAAGGTCACCGGCA
CGCTGCCTGCCCAGTGGAGCTCGATGACGTCGCTGGACAAACCTTAACCTGCACGACACGGCGGTCT
CCGGCACGCTGCCTGCCCAGTGGAGCTCGATGAAGCAGCGACCGTTCTGGATCTGGAGGGCACTA
AGGTGTCCGGCACGCTGCCGTCCGAGTGGAGTGGGATGGCGAAGGCCGAGGCCGGTGCAGCTGCAG
AACTGCGGTCTGTCCGGGAGTCTGCCCCCCTCGTGGTCTGCGATGCCGAAGCTGCGTATCGTCTCAC
TGAGCGGCAACGACTTCTGCGGGTGCGTGCCCGACTCGTGGAGGGAGAAGGACGGCCTCGATGTG
ACCATCGAGGAATGGCACATGGGCGAGGACTGCAAGCTTGCTAACGCCTGCCGCCCGACTGCTGCT
CCGGGAACGACCACGACTAACCCGCCGCCACCACCACCGGCACCGCAGCAGCCTCCTCTACTCCTTCT
CCAGGGTCGGGGTGCGAGGTGGATGGGTGTGAGGTGTGCGAGGGGGACTCGGCTGCGCGGTGCGC
CAGGTGCCCGTGAGCGCTACTCCCTGACGGACGAGAAGACGTGCCTGGCGAACGACGATGCGGCG
TGGCGGCGGCGTCGAGCGGAGCGGTGGCTGCCGCTGCTGTGTGGGCGGCTGTGGTGTTGAGCGTGG
GGCTGGTGGCGTGAGGGTGCGGCGGGCCGCTCTTCTCTGTGGTGCCCCTGGTCCCTGCCCTCGCCC
CCGGCACGGCGTCGTCGCTGCCCTCTCTCACCCCCACCAGCCGACGGGGAGACCGACAGCCACACG
CGCACGCGCACACGCCGTCGTGCATGGCGTGTGCTTTCCGCCGTTGTGGCGCCTGCAGGGATGCAC
GGGCATGCGGAGGCGTGCATGCGTGTGCGCGTGCCAGCTGTTGTGTGTCTGTCCGTGTGGCCAGCA
GTCGGCACCCCGCCGATCGAATGTGCGCGCGGCGGCGGTGGTCCGCGTTGGACAGCGGATGCGG
GCGCCCGCCCCTCGCCGTGTGCCCTGGGGTCTGCTGTGCTGCCGCGCGAGCGACGTAAGGATGCGC
TGTCCGGCCCTCTTCGACGGGCTCGCTTGCGGTGCTGTGCTCTCGTGGTCTGTGCGGTGCTGCTC
TGGCGGGGTGAGAGCTGGCGGCGGGCGTGGGTGCGCGCGCGGCAGCTCTCCGCTGCGTTGAGGGCG
GCCTGCCCCTGCGTCCGCGCACCGTCGCGCTCTCCTCGACGCCACTGCGCGCGCTTGTTGGCTTGCT
TTGCTCTGTCGTGCGCACTCTCTCTTATTTTCCGTTTCATTCGCCTGTATTCTCTTCTCCCACCGCACT
GCGGCCTCGTCACCGCGGCCGTGCGGTGCGCAGGCGGGTGATGTGCCGTTGTGCCCCCCCTTTCAT
GGCGCGCTGGGCCGATCGCCCTCTTGCCTCCCTCCTCGCCCCTCCCCCTCCCGCCGGTCCTGTCAATT
GTATATCCGTGGACCTTATCTTCGTACTGCCTCCGCGCCTCTTCCGTAAAGCTTCGTTGGCGTGTGC
CCCCCCCCGGACGTCAGCGCCGCTGTGCTCGCATGCTCACGGTGCGTCCCCGTGCGTGGGCGTGCA
CGTAAGGACATGTATATATGTATGTGTATGTATATGAGTATGTATATATGTACGGTTATATATAGGA
ATTTGTGTATGTTGAGGTGTATGCATGTGCGTGCGTATATTAGTGTGTGCGAGCACGCGTGTTGCGC
CACGCTCTGCTGCCCGCCTCCGCTGTGCGTGTCACTCGCTGTGGCGCGGTGGCGGGTGGCGCCGG
GTGGTGGCCGTGCGGCGGCGGGGGCTCCTCTGTGTTTCTCTATTTCTCTGTTTCCCTGTTGACCTCA
AAAAAAAAAAAAAAAAAAAAAA
```

SEQ ID No 2 (Nucleic sequence 2CI)

```
CGTGGACGGGCAGCGACTTCTGCTCGTGGAAGCACATCATCTGCGACTGCCCCGGCGTCGGCGTGT
GGATGGGCGATGTGGATTATACCGGCACGCTGCCGGAGATGCCTGCGAGCGTCGACTACAAGGAC
GTCATGATCACGGAACTGAACTTCAGCGCAATGGGCCAGGGGCTGAGCGGGACGCTGCCCCCCTC
ATGGAGCTCGCTGACGTCCTTGATATCACTGTGCATCGAAAAGTCTGAGAAGGTCACCGGCACGCT
GCCTGCCCAGTGGAGCTCGATGACGTCGCTGGACAAACCTTAACCTGCAGGACACGGCGGTCTCGG
CACGCTGCCTGCCCAGTGGAGCTCGATGAAGCAGCTGACCGTTCTGGATCTGGAGGGCACTAAGGT
GTCCGGCACGCTGCCGTCCGAGTGGAGTGGGATGGCGAAGGCCGAGGCCGTGCAGCTGGAGAACT
GCGGTCTGTCCGGGAGTCTGCCCCCCTCGTGGTCTGCGATGCCGAAGCTGCGTATCGTCTCACTGA
GCGGCAACCACTTCTGCGGGTGCGTGCCCGACTCGTGGAGGGAGAAGGACCGCCTCGATGTGACC
ATCGAGGAATGGCACATGGGCGAGGACTGCAAGCTTGCTAACGCCTGCCGCCCGACTGCTGCTCCG
GGAACGACCACGACTAACCCGCCCACCACCACCGGCACCCCAGCAGCCTCCTCTACTCCTTCTCCA
GGGTCGGGGTGCGAGGTGGATGGGTGTGAGGTGTGCGAGGGGGACTCCGCTGCGCGGTGCGCCAG
GTGCCGTGAGGGCTACTCCCTGACGGACGAGAAGACGTGCGTGGCGAACCACGATGGCGGCGTGG
CGGCGGCGTCGAGCGGAGCGGTGGCTGCCGCTGCTGTGTGGGCGGCTGTGCTGTTGAGCGTGGGGC
TGGTGGCGTGAGGGTGCGGCGGGCCCCTCTTCTCTGTGGTGCCCCTGGTGCCTGCCCTCGCCCCG
GCACGGCGTCGTCGGTGCCCTCTCTGACCCCCACCAGCCGACGGGGAGACCGACAGCCACACGCGC
ACGCGCACACGCCGTCGTGCATGGCGTGTGC
```

Figure 7

SEQ ID No 3 (Nucleic sequence 1A1)

```
GGACGGGCAGCGACTTCTGCTCGTGGAAAGCACATCATCTGCGACTCCCCGGGCGTCGGCGTGTGGA
TGGGCGATGTGGATTATACCGGCACGCTGCCGGAGATGGCTGCGAGCGTCGACTACAAGGACGTC
ATGATCATGGCACTGGACTTCGGCGCAATGGGCCAGGGACTCAGCGGGACGCTGCCCCCCTCATGG
AGCTCGCTGACGTCCTTGATGTCACTGTGGATGGAAAAGTCTGAGAAGGTCACCGGCACGCTGCCT
ACCCAGTGGAGCTCGATGAAGCAGCTGACCCTTCTGCATCTGAAGGGCACTAAGGTGTCCGGCAGG
CTGCCGCCCGAGTGGAGTGGGATGACGTCGCTGGACGACCTTAACCTGCACGACACGGCGGTCTCC
GGCACGCTGCCTGCCCAGTGGAGCTCGATGAAGCAGCTGATCGATCTGCATCTGGAGGGCACTAA
GGTGTCCGGCACGCTGCCGCCCGAGTGGAGTGGGATGGGGAAGGCCGAGGCCCTGCAGCTGAAGT
ACTGCGATCTGTCCGGCAGTCTGCCCCCCTCGTGGTCTTCGATGCAGAAGCTGCGTATCGTCTCACT
GAGCGGCAACCACTTCTGCGGGTGCGTGCCGCGACTCGTGGAGGGAGAAGGACCGCCTCGATGTGA
CCATCGAGGAATGGCACATGGGCGAGGACTGCAAGCTTGCTAACGCCTGCCGCCCGACTGCTGCTC
CGGGAACGACCACGGACTAACCCGCCCACCACGACCGGCACCCCAGCAGCCGGCTCTACTCCTTCTC
CAGGGTCGGGGTGCGAGGTGGATGGGTGTGAGGTGTGCCAGGGGGACTCCGCTGCGCGGTGCGCC
AGGTGCCGTGAGGGCTACTCGCTCAGGGACGAGAAGACGTGCCTGGCGAACCACGATGGCGGCGT
GGCGGCGGCGTCGAGCGGAGCGGTGGCTGGCGGCTGCTGTGTGGGCGGCTGTGCTGTTGAGCGTGG
GGCTGGTCGCGTGAGGGTGCGGCGGCCCCCTCTTCTCTGTGGTGCCCCGTGGTGCCTGCCCTCGCGC
CCAGCACGGCGTCGTCGCTGCCCTCTCACCCGCACCAGCCGAAGGGGAGACCGACAGCCACACGG
ACACGCGCACGGCCGGTCGTGCATCGCGTGTGCTTTCCGCCGTTGTGGGGCGTGCGCGGATGCACG
GGCATGCGGAGGCGTGCATGCGTGTGCGCGTGCCACTCTTGTGTGTCTCTCCGTGTGGCCAGCAG
TCGGCACCCGGCGGATCGAATGTGCCGCGCGGCGGCGTGTGTCGGCCTGGAGAGCCGGATGCGGC
GCCCGCCCCTCGCCGTGTGCCCTGCGGTCTGCTGTGCTGCGGCCGAGCGACGTACGGA
```

SEQ ID No 4 (Nucleic sequence 2G1)

```
TCGGCGTGTGGATGGGCGATGTGGATTATACCGGCACGCTGCCGGACATGCCTGCGAGCGTCGACT
ACAAGGACGTCATGATCACGGAACTGAACTTCGGCGCAATGGGCGAGGGACTGACCGGGACGCTG
GCCGCGTCATGGAGGTCGATGAAGCAGCTGATCGATGTGGATGTGGAGGGCACTAAGGTGTGCGGC
ACGCTGCCGCCGAGTGGAGTGGGATGGCGAAGGCCGAGGCCCTGCACGTGAAGTACTGCGATCT
GTCCGGCAGTCTGCCCCCCTCGTGGTCGTCGATGCAGAAGCTGCGTATCGTCACTGAGCGGCAA
CCACTTCTGCGGGTGCGTGCCGGACTCGTGGAGGGAGAAGGACGGCCTCGATGTGACCATCGAGG
AATGGCACATGGGCGAGGACTGCAAGCTTGCTAACGCCTGCCGCCCGACTGCTGCTCCGGGAACG
ACCACGACTAACCGGCCCACCACCACGGCAGCCCAGCAGCCGTCCTCTACTCCTTCTCCAGGGTCG
GGGTGCCGAGGTGGATGGGTGTGAGGGTGTGCGAGGGGGACTCCGCTGCCGGTGCCCAGGTGCGG
TGAGGGCTACTCCCTGACGGACGAGAAGACGTGCCTGGCGAACCACGATGGCGGCGTGGCGGCGG
CGTCAAGCGGAGCGGTGGCTGCGGCTGCTGTGTGGGCGGCTGTGCTGTTGAGGGTGGGGCTGGGG
CGTCAGGGTGCGGCGGGCCCCTCTTCTCTGTGGTGCCCCGTGGTGGCTGCGCTGCCCCGCACGG
CCTCGTCGCTGCCCTCTCTCACGCCCACCAGCCGACGGGGAGACGGACAGC
CACACGCGCACGCGCACACGCCGTCGTGCATCGCGTGTGCTTCCGCCGTTGTGGCGCCTGGACGG
ATGCACGGGCATGCGGAGGCGTGCATGCGTGTGCGGGTGCCAGCTCTTGTGTGTCTCTCCGTGTGG
CCAGCAGTCGGCACCCGCGCCGATCGAATGTGCCGCGGCGGCGGTGGTGTCGCCTTGGACAGCGG
ATGCTGGCGCCCGCCCCTCGCGTGTGCCTCGGTCTGCCTGTCGTGGCCGCGCGAGCGACGTACGGA
GTGCGCTGTCGCCGGGTGGTGGCCGTGCCGGCGGGCGGGGGCTCCTCTGTGTTTCTCTATTTCTCTGT
TCCCTGTTGACCTCAAAAAAAAAAAAAAAAAAAAAA
```

Figure 7 (continued)

SEQ ID No 5 (Nucleic sequence W2)

CCGGCGTCGGCGTGTGGATGGGCGATGTGGATTATACCGGCACGCTGCCGGAGAT
GCCTGCGAGCGTCGACTACAAGGACGTCATGATCACGGAACTGAACTTCAGCGC
AATGGGCCAGGGGCTGAGCGGGACGCTGCCCCCTCATGGAGCTCGCTGACGTCC
TTGATATCACTGTGCATCGAAAAGTCTGAGAAGGTCACCGGCACGCTGCCTGCCC
AGTGGAGCTCGATGACGTCGCTGGACAACCTTAACCTGCACGACACGGCGGTCTG
CGGCACGCTGCCGCCCGAGTGGAGTGGGATGACGTCGCTGGACGACCTTAACCTG
CACGACACGGCGGTCTCCGGCACGCTGCCTGCCCAGTGGAGCTGGATGAAGCAG
CTGATCGATCTGGATCTGGAGGGCACTAAGGTGTCCGGCACGCTCCGCCCGAGT
GGAGTGGGATGGCGAAGGCCGAGGCCCTGCAGCTGAAGTACTGCGATCTGTCCG
GGAGTCTGCCCCCCTCGTGGTCTTCGATGCAGAAGCTGCGTATCGTCTCACTGAG
CGGCAACCACTTCTGCGGGTGCGTGCCGGAGTCGTGGAGGGAGAAGGACCGCCT
CGATGTGACCATCGAGGAATGGCACATGGGCGAGGACTGCAAGCTTGCTAACGC
CTGCCGCCCGACTGCTGCTCCGGGAACGACCACGACTAACCCGGCCACCACCACC
GGCACCCCAGCAGCCTCCTCTAGTGCTTCTCCAGGGTCGGGGCTGCCAGGTGG
ATGGGTGTGAGGTGTGCGAGGGGGACTCCGCTGCGCGGTGCGCCAGGTGCCGTG
AGGGCTACTCCTGACGGACGAGAAGACGTGGCTGGCGAAACCACGATGGCGGCGT
GGCGGCGGCGTCAAGCGGAGCGGTGGGTGCGGCTGCTGTGTGGGCGGCTGTGCT
GTTGAGCGTGGGGCTGGTGGCGTGAGGGTGCCGGCCGCCGCTGTTCTCTGTGGTG
CCCCTGGTGCCTGCCCTCGCCCCCAGCACGGGGTCGTCGCTGCCTCTCACGCCCA
CCAGCCGAAGGGGAGACCGACAGCCACACGGACAGGCGCACGGCGCCGTGGTGCA
TCGCGTGTGCTTTCCGCCGTTGTGGCGCCTGCGGGGATGCACGGGCATGCGGAGG
CGTGCATGCGTGTGCGGGTGCCAACTCTTGTGTGTCTCTGCGTGTGGCCAGCAGTC
GGCACCC

Figure 7 (continued)

SEQ No 11 (Nucleic sequence IJ11 of Ldi)

```
GCGCTGCTGCCGCTGGCGCTGTTGTGTGTGCTGGGGCCGCGCCACGCA
CACGCACGGTAGTGAGGGGGAGCCGCAGCGACCGACCGGGCGGAGCGGGC
GGGCGGAGGGGGCGCTCCCGCCCGCTGGTCATGCTCTCTGTTTCGCTGG
CCGGCCTCTCTACGCCGCTGGCGTGGGCGGAGCTCCGCGCTGCGTATCGC
TCGCCCCTCGCTGCCCCTCCCTGCCCCTCCTCATGTGCACTGCTCCCTCC
CTCTCCCTCCCTCTACACTCCTCGCTGTCCCCTCGGCCGACCTCCACGGA
CACGCAGACGTGCGTGCGCATACACACCACCCCTCACCTCGCTGCTGCTG
CTGTGACAGCTCTACGGACCCTGCCCAGTCGCTGCGCCCCGCCACCCGC
CTCTGTCCCCCGCACGAGGGTACCTACGACGTGCCGGCCACCCCGCTCTG
CCCGATAAGCTGAGCTGGCGCTCACGCCCGAGCAATCCCCTCACGGATCT
GCTGCCGCGCCGCACTGCTCTTGACCCTGGCTGCGAATGGCGCTGTGCGT
GCGTCGGCTGGTGCTGGCGGCGACCCTCGCCGCTGTGGTGGCGCTGCTGC
TGTGCACGAGCAGTGCGCCGGTGGCGCGTGCTGCTGTGAAGGATGACTTC
ACTGCTGCGCAGCGGACGAACACGCTGGCGGTGCTGGAGGCGTTTCGGCG
TGCGATCCCTGAGCTTGGGAAGCTGTGGAAGGGCGACGACTTCTGC
TTTTGGGAGTCGGTCGTGTGCGATGTGACCGAAGTGTACTTGTGGGAA
ATCGGTGCGACGTATACCGGCACGCTGCCGGAGATGCCTGTGGACGTCGA
CTACACGGCCGTCATGGTCAAGCACCTCGACTTTTCCCAAATGGGGCTGG
GGCTGAGCGGAACGCTGCCGGACAGCTGGAGCAGGCTGCAGGGACTGACC
TCACTTACGTTGTCGGGCTGCGGCGTGAGCGGTACGCTGCCCCCCTCGTG
GCGCTCGATGAAGTCTTTGGTGTCGTTGTGGATTGAGAGTTGTGAAAGTG
TTACCGGCAAGCTGCCGCCTGAGTGGAGCTCGATGAAATCGCTGAGAGAT
CTCCATCTGCATGGCGCGAAGGTTTCCGGCACGCTGCCGCCTGAGTGGAG
CACGATGAAATCGCTGACCCTTCTCGATCTGCAGGACACTCAGGTTACCG
GCAGTCTGCCGCCTGAGTGGAGCTCAATGAAATCCATGACCATTCTCAGT
CTGAATGGCGCGAAGGTTTCCGGCACGCTGCCACCCCAGTGGAGCTCGAT
GACATCGCTGAGCCTTCTCAGTCTGGAGGGTACTCAGCTCTCCGGCACGC
TACCGCCCAGTGGAGTGGGATGACATCGCTGGTCACGCTTTTCTGCA
GGGTACTCAGGTCTCCGGCACTCTGCCGCCGCAGTGGAGATCGATGTTGAA
TGCCGAGTTCCTGCAGCTGGAGAACTGCGACCTGTCCGGCTGTTTGCCCCC
CGAGTGGGCTGCGATGCCGAAGCTGCGTCATGTCGAACTTAAGGGCAACCA
GTTCGCCGGGTGTGTGCCGGACTCGTGGGCTCAGAAGGCCGGTCTCGTTGT
GGAAATCGAGGATAAGCACACGGGCAACAGCTGCATTGCTGGTGCGGACTG
CGCAACGACGACCACGACCACCACTGAACCCACGTCCACTGCGAGCCCAAC
AGCCACGCCTACCTCTGCCCCCGAGACGGAGTGCGAGGTGGATGGGTGTGA
GGTGTGCGATGGGGACTCCGCGGCGAGGTGCGCCAGGTGCCGTGAGGGCTA
CTTCCTGACGGACGAGAGGACGTGCCTGGTGTACCGCGATGGCGGCGTTGT
GGCCGTGTCGATCGGAGCGGCTGCTGCCGCTGTTGTGTGCATGGCTGTGCT
GCTGAGCGTGGGGCTGGCGGCGTGAGGATGCCGCTGCTGTCGCGCGCAGGC
GGCGGCACCCGCTGCGTGGCACACGACTGCGTGCTTGCGTGCAGCACCGCG
CCCTGCATTGGCGTGCGTGTGCGCGTCTGTGTGTGCATGGCTGCTGACGGT
GCCTTTCGTCCTGCCTCTCGCTGCCTCTGCCTCTCTCCGCGTGTGAATGCT
GTGGGCTGTGTTTGGGGCTCTCGTGCGGCGCTGCTGTACGGCTGCTGCTTC
TTCTCCACCCTCCTCTCTCGCATGCCGGCGAGGGAGGGGTGGCACGTGCGC
GTGTGCCGCTGCGCTTGCGAGTGCGTCTGTGTGTGGGCCTTCACCACGTGC
```

Figure 7 (continued)

```
TACGGTCACGCCTTCTCGGCTGGCCACTCGCGGCGCTGAGGGCGGTGTGCC
CTTCCCCTCGAGCGCCGTCGCACTCTCTTCCGCGCGCCTGCGCGGGCTTCT
TCGTGCGCTGTGCTCAGCCGTGCGCTCTCACCTCTTTCCCTTTTCATTCGC
TTGTCTTCTCTCTTCTCCCCCCGCAETGCGGTCTCCCCTCCTCTGCCGTGC
GGTGCGCAGGCGGGTGACTTGCCGTTGCGTCTCCCCCTTTCGTGGAGCGCT
GAGCCGATCCCCCTTCGGCCTCCCTCCTCCCTCCTCCCGTGGGTCCTGTCT
GTTGTACATCGTCGGACCGTCTCTTCGTGTTGCCTCTCCGCACCTTCCGCA
AATCTGCGCTCGCCTGTGCCGCCTCTCGGACTTTATCCTTACTGTGATTGT
ATTCTCACGGTGCGTCTCCGTGTGTGTGTGCCACGCACCGCTTCTTCCA
TGTGTGTCCTTGCTTGCTCTCGTCTGCCCCCCCCCCTCTGCCTCACACATT
CCGTGCGTGTGTGCATCACCGTTGGGCGGCGACATCGGTGCCCGTCCCTGC
CACCCTCTACTCCCTCATTCTCTTGCCACTTCGTGGGCGGTGCGTGCATGC
ATGGATGTATATACACGCATAGAGGGGTGGGGACGCGGGGGATCCTCTAGA
GTCGACCTGCAGGCATGCAAGCTTGGCGTAATCATGGTCATAGCTGTTTCC
TGTGTGAAATTGTTATCCGCTCACAATTCCACACAACATACGAGCCGGAAG
CATAAAGTGTAAAGCCTGGGGTGCCTAATGAGTGAGCTAACTCACATTAAT
TGCGTTGCGCTC
```

Figure 7 (continued)

SEQ No 6 (Protein sequence A3B)  (sense direction)  372 aa
MAQCVRRLVLAAPLAAVVALLLCTSSAPVARAAGTSDFTEAQQTNTLTVLQAFARAIPAL
GDTWTGSDFCSWKHIICDSPGVGVWMGDVDYTGTLPEMPASVDYKDVMITELNFSAMGQG
LSGTLPPSWSSLTSLISLCIEKSEKVTGTLPAQWSSMTSLDNLNLHDTAVSGTLPAQWSS
MKQLTVLDLEGTKVSGTLPSEWSGMAKAEAVQLENCGLSGSLPPSWSAMPKLRIVSLSGN
HFCGCVPDSWREKDRLDVTIEEWHMGEDCKLANACRPTAAPGTTTTNPPTTTGTPAASST
PSPGSGCEVDGCEVCEGDSAARCARCREGYSLTDEKTCLANHDGGVAAASSGAVAAAVW
AAVLLSVGLVA*

SEQ No 7 (Protein sequence 2CI)  (sense direction)  287 aa
MGDVDYTGTLPEMPASVDYKDVMITELNFSAMGQGLSGTLPPSWSSLTSLISLCIEKSEK
VTGTLPAQWSSMTSLDNLNLHDTAVSGTLPAQWSSMKQLTVLDLEGTKVSGTLPSEWSGM
AKAEAVQLENCGLSGSLPPSWSAMPKLRIVSLSGNHFCGCVPDSWREKDRLDVTIEEWHM
GEDCKLANACRPTAAPGTTTTNPPTTTGTPAASSTPSPGSGCEVDGCEVCEGDSAARCAR
CREGYSLTDEKTCVANHDGGVAAASSGAVAAAVWAAVLLSVGLVA*

SEQ No 8 (Protein sequence 1AI)  (sense direction)  311 aa
MGDVDYTGTLPEMPASVDYKDVMINALDFGAMGQGLSGTLPPSWSSLTSLMSLWIEKSEK
VTGTLPTQWSSMKQLTLLHLKGTKVSGTLPPEWSGMTSLODLNLHDTAVSGTLPAQWSSM
KQLIDLDLEGTKVSGTLPPEWSGMAKAEALQLKYCDLSGSLPPSWSSMQKLRIVSLSGNH
FCGCVPDSWREKDRLDVTIEEWHMGEDCKLANACRPTAAPGTTTTNPPTTTGTPAASSTP
SPGSGCEVDGCEVCEGDSAARCARCREGYSLTDEKTCLANHDGGVAAASSGAVAAAAVWA
AVLLSVGLVA*

SEQ No 9 (Protein sequence 2G1)  (sense direction)  238 aa
MGDVDYTGTLPEMPASVDYKDVMITELNFGAMGQGLSGTLPPSWSSMKQLIDLDLEGTKV
SGTLPPEWSGMAKAEALQLKYCDLSGSLPPSWSSMQKLRIVSLSGNHFCGCVPDSWREKD
RLDVTIEEWHMGEDCKLANACRPTAAPGTTTTNPPTTTGTPAASSTPSPGSGCEVDGCEV
CEGDSAARCARCREGYSLTDEKTCLANHDGGVAAASSGAVAAAVWAAVLLSVGLVA*

SEQ No 10 (Protein sequence W2)  (sense direction)  271 aa
MGDVDYTGTLPEMPASVDYKDVMITELNFSAMGQGLSGTLPPSWSSLTSLISLCIEKSEK
VTGTLPAQWSSMTSLDNLNLHDTAVSGTLPPEWSGMTSLDDLNLHDTAVSGTLPAQWSSM
KQLIDLDLEGTKVSGTLPPEWSGMAKAEALQLKYCDLSGSLPPSWSSMQKLRIVSLSGNH
FCGCVPDSWREKDRLDVTIEEWHMGEDCKLANACRPTAAPGTTTTNPPTTTGTPAASSTP
SPGSGCEVDGCEVCEGDSAARCARCREGYS*

SEQ No 12 (Protein sequence IJ11 of Ldi)  (sense direction)  464 aa
MALCVRRLVLAATLAAVVALLLCTSSAPVARAAVKDDFTAAQRTNTLAVLEAFG
RAIPELGKLWKGDDFCFWESVVVRCDRSVLGGKSVRRIPARCRRCLWTSTTRPSW
SSTSTFPKWGWGWAERCRTAGAGCRDWPHLRCRAAAWAYRCPPRGARWSLWCR
CGLRVVKVLPASCRLSGARWNRWEISICMARRFPARCRLSGARWNRWPFSICRTL
RLPAVCRLSGAQWNPWPFSVWMARRFPARCHPSGARWHRWAFSVWRVLSSPAR
YRPSGSGMTSLVTLFLQGTQVSGTLPPQWRSMLNAEFLQLENCDLSGCLPPEWAA
MPKLRHVELKGNQFAGCVPDSWAQKAGLVVEIEDKHTGNSCIAGADCATTTTTT
EPTSTASPTATPTSAPETECEVDGCEVCDGPSAARCARCREGYFLTDERTCLVYRD
GGVVAVSIGAAAAAVVCMAVLLSVGLAA*

Figure 7 (continued)

SEQUENCE LISTING

<160> NUMBER OF SEQ ID NOS: 12

<210> SEQ ID NO 1
<211> LENGTH: 2526
<212> TYPE: DNA
<213> ORGANISM: Leishmania amazonensis

<400> SEQUENCE: 1

```
gacccctgtt gcgaatggcg cagtgcgtgc gtcggctggt gctggcggcg cccctcgccg      60
ctgtggtggc gctgctgctg tgcacgagca gtgcaccggt ggcgcgtgct gcggggacga     120
gcgacttcac tgaggcgcag cagacgaaca cgctgacggt gctgcaggcg tttgcgcgtg     180
cgatccctgc gcttggggac acgtggacgg gcagcgactt ctgctcgtgg aagcacatca     240
tctgcgactc ccccggcgtc ggcgtgtgga tgggcgatgt ggattatacc ggcacgctgc     300
cggagatgcc tgcgagcgtc gactacaagg acgtcatgat cacggaactg aacttcagcg     360
caatgggcca ggggctgagc gggacgctgc cccctcatg gagctcgctg acgtccttga     420
tatcactgtg catcgaaaag tctgagaagg tcaccggcac gctgcctgcc cagtggagct     480
cgatgacgtc gctggacaac cttaacctgc acgacacggc ggtctccggc acgctgcctg     540
cccagtggag ctcgatgaag cagctgaccg ttctggatct ggagggcact aaggtgtccg     600
gcacgctgcc gtccgagtgg agtgggatgg cgaaggccga ggccgtgcag ctggagaact     660
gcggtctgtc cgggagtctg cccccctcgt ggtctgcgat gccgaagctg cgtatcgtct     720
cactgagcgg caaccacttc tgcgggtgcg tgcccgactc gtggagggag aaggaccgcc     780
tcgatgtgac catcgaggaa tggcacatgg gcgaggactg caagcttgct aacgcctgcc     840
gcccgactgc tgctccggga acgaccacga ctaacccgcc caccaccacc ggcaccccag     900
cagcctcctc tactccttct ccagggtcgg ggtgcgaggt ggatgggtgt gaggtgtgcg     960
aggggggactc cgctgcgcgg tgcgccaggt gccgtgaggg ctactccctg acggacgaga    1020
agacgtgcct ggcgaaccac gatgcggcg tggcggcggc gtcgagcgga gcggtggctg    1080
ccgctgctgt gtgggcggct gtgctgttga gcgtggggct ggtggcgtga gggtgcggcg    1140
ggcacacgcg cacgcgcaca cgccgtcgtg catcgcgtgt gctttccgcc gttgtggcgc    1200
ctgcacggat gcacgggcat gcggaggcgt gcatgcgtgt gcgcgtgcca gctcttgtgt    1260
gtctctccgt gtggccagca gtcggcaccc gcgccgatcg aatgtgcgcg cggcggcggt    1320
gtgtcgcctt ggacagcgga tgcgggcgcc cgccctcgc cgtgtgccct gcggtctgct    1380
gtgctgccgc gcgagcgacg tacggatgcg ctgtccggcc ctcttcgacg gggctcgctt    1440
gcggtgctgt gctctcgtgg tctgtgccgg tgctgccctg gcggggtgag agctggcggg    1500
ggcgtgggtg cgcgcgcggc agctctccgc tgcgttgagg gcggcctgcc cctgcgtccg    1560
cgcaccgtcg cgctctcctc gacgccactg cgcgcgcttg ttggcttgct ttgctctgtc    1620
gtgcgcactc tctcttattt tccgtttcat tcgcctgtat tctcttctcc caccgcactg    1680
cggcctcgtc accgcggccg tgcggtgcgc aggcgggtga tgtgccgttg tgccccccct    1740
ttcatggcgc gctgggccga tcgccctctt gcctccctcc tcccctcc cctcccgccg    1800
gtcctgtcaa ttgtatatcc gtggacctta tcttcgtact gcctccgcgc ctcttccgta    1860
aagcttcgtt ggcgtgtgcc gcccccgga cgtcagcgcc gctgtgctcg catgctcacg    1920
gtgcgtcccc gtgcgtgggc gtgcacgtaa ggacatgtat atatgtatgt gtatgtatat    1980
gagtatgtat atatgtacgg ttatatatag gaatttgtgt atgttgaggt gtatgcatgt    2040
```

-continued

| | |
|---|---|
| gcgtgcgtat attagtgtgt gcgagcacgc gtgttgcgcc acgctctgct gcccgcctcc | 2100 |
| gctgtgcgtg tcactcgctg tgggcgcggt ggcgggtggc gccgggtggt ggccgtgcgg | 2160 |
| cgggcggggg ctcctctgtg tttctctatt tctctgttcc ctgttgacct caaaaaaaaa | 2220 |
| aaaaaaaaaa aaagtgcacg taaggacatg tatatatgta tgtgtatgta tatgagtatg | 2280 |
| tatatatgta cggttatata taggaatttg tgtatgttga ggtgtatgca tgtgcgtgcg | 2340 |
| tatattagtg tgtgcgagca cgcgtgttgc gccacgctct gctgcccgcc tccgctgtgc | 2400 |
| gtgtcactcg ctgtgggcgc ggtggcgggt ggcgccgggt ggtggccgtg cggcgggcgg | 2460 |
| gggctcctct gtgtttctct atttctctgt tccctgttga cctcaaaaaa aaaaaaaaaa | 2520 |
| aaaaaa | 2526 |

<210> SEQ ID NO 2
<211> LENGTH: 1401
<212> TYPE: DNA
<213> ORGANISM: Leishmania amazonensis

<400> SEQUENCE: 2

| | |
|---|---|
| cgtggacggg cagcgacttc tgctcgtgga agcacatcat ctgcgactcc cccggcgtcg | 60 |
| gcgtgtggat gggcgatgtg gattataccg gcacgctgcc ggagatgcct gcgagcgtcg | 120 |
| actacaagga cgtcatgatc acggaactga acttcagcgc aatgggccag ggctgagcg | 180 |
| ggacgctgcc cccctcatgg agctcgctga cgtccttgat atcactgtgc atcgaaaagt | 240 |
| ctgagaaggt caccggcacg ctgcctgccc agtggagctc gatgacgtcg ctggacaacc | 300 |
| ttaacctgca cgacacggcg gtctccggca cgctgcctgc ccagtggagc tcgatgaagc | 360 |
| agctgaccgt tctggatctg gagggcacta aggtgtccgg cacgctgccg tccgagtgga | 420 |
| gtgggatggc gaaggccgag gccgtgcagc tggagaactg cggtctgtcc gggagtctgc | 480 |
| cccctcgtg gtctgcgatg ccgaagctgc gtatcgtctc actgagcggc aaccacttct | 540 |
| gcgggtgcgt gcccgactcg tggagggaga aggaccgcct cgatgtgacc atcgaggaat | 600 |
| ggcacatggg cgaggactgc aagcttgcta acgcctgccg cccgactgct gctccgggaa | 660 |
| cgaccacgac taacccgccc accaccaccg gcacccagc agcctcctct actccttctc | 720 |
| cagggtcggg gtgcgaggtg gatgggtgtg aggtgtgcga gggggactcc gctgcgcggt | 780 |
| gcgccaggtg ccgtgagggc tactccctga cggacgagaa gacgtgcgtg gcgaaccacg | 840 |
| atggcggcgt ggcggcggcg tcgagcggag cggtggctgc cgctgctgtg tgggcggctg | 900 |
| tgctgttgag cgtggggctg gtggcgtgag ggtgcggcgg gccctcttc tctgtggtgc | 960 |
| ccctggtgcc tgccctcgcc cccggcacgg cgtcgtcgct gccctctctc accccacca | 1020 |
| gccgacgggg agaccgacag ccacacgcgc acgcgcacac gccgtcgtgc atcgcgtgtg | 1080 |
| cgtgcactta aggacatgta tatgtgtatg tgtatgtata tgagtatgta tatgtgtccg | 1140 |
| gttatatata ggaatttgtg tatgttgagg tgtatgcatg tgcgtgcgta tattagtctg | 1200 |
| tgcgagcacg cgtgttgcgc cacgctttgc tgcccgcctc cgctgtgcgt gtccctccct | 1260 |
| gtgggcgcgc tgccgggtgg ccccgggtgg tgccgtgcg gcgggcgggg gctcctctgt | 1320 |
| gtttctctat ttctctgttc cctgttgacc ccaaaaaaaa aaaaaaaaaa aaaaaaaaaa | 1380 |
| aaaaaaaaaa aaaaaaaaaa a | 1401 |

<210> SEQ ID NO 3
<211> LENGTH: 1684
<212> TYPE: DNA
<213> ORGANISM: Leishmania amazonensis -continued

```
<400> SEQUENCE: 3
ggacgggcag cgacttctgc tcgtggaagc acatcatctg cgactccccc ggcgtcggcg      60
tgtggatggg cgatgtggat tataccggca cgctgccgga gatgcctgcg agcgtcgact     120
acaaggacgt catgatcatg cactggact tcggcgcaat gggccaggga ctgagcggga      180
cgctgccccc ctcatggagc tcgctgacgt ccttgatgtc actgtggatc gaaaagtctg     240
agaaggtcac cggcacgctg cctacccagt ggagctcgat gaagcagctg acccttctgc     300
atctgaaggg cactaaggtg tccggcacgc tgccgcccga gtggagtggg atgacgtcgc     360
tggacgacct taacctgcac gacacggcgg tctccggcac gctgcctgcc cagtggagct     420
cgatgaagca gctgatcgat ctggatctgg agggcactaa ggtgtccggc acgctgccgc     480
ccgagtggag tgggatggcg aaggccgagg ccctgcagct gaagtactgc gatcgtccg      540 ggagtctgcc cccctcgtgg tcttcgatgc agaagctgcg tatcgtctca ctgagcggca     600
accacttctg cgggtgcgtg cccgactcgt ggagggagaa ggaccgcctc gatgtgacca     660
tcgaggaatg cacatgggc gaggactgca agcttgctaa cgcctgccgc ccgactgctg      720
ctccgggaac gaccacgact aacccgccca ccaccaccgg caccccagca gcctcctcta     780
ctccttctcc agggtcgggg tgcgaggtgg atgggtgtga ggtgtgcgag ggggactccg     840
ctgcgcggtg cgccaggtgc cgtgagggct actccctgac ggacgagaag acgtgcctgg     900
cgaaccacga tggcggcgtg gcggcggcgt cgagcggagc ggtggctgcg gctgctgtgt     960
gggcggctgt gctgttgagc gtggggctgg tggcgtgagg gtgcggcggc ccctcttct    1020 ctgtggtgcc cctggtgcct gccctcgccc ccagcacggc gtcgtcgctg ccctctcacc    1080
cccaccagcc gaaggggaga ccgacagcca cacgcacacg cgcacgcgcc gtcgtgcatc    1140
gcgtgtgctt tccgccgttg tggcgcctgc gcggatgcac gggcatgcgg aggcgtgcat    1200
gcgtgtgcgc gtgccagctc ttgtgtgtct ctccgtgtgg ccagcagtcg gcacccgcgc    1260
cgatcgaatg tgcgcgcggc ggcggtgtgt cgccttggac agcggatgcg gcgcccgccc    1320
ctcgccgtgt gccctgcggt ctgctgtgct gccgcgcgag cgacgtacgg agtgcatgta    1380
aggacatgta tatatgtatg tgtaggtata tgagtatgta tatatgtacg gttatatata    1440
ggaatttgtg tatgttgagg tgtatgcatg tgcgtgcgta tattagtctg tgcgagcacg    1500
cgtgttgcgc cacgctttgc tgcccgcctc tgctgtgcgt gtcactccct gtgggcgcgc    1560
tggcgggtgg cgccgggtgg tggccgtgcg gcgggcgggg gctcctctgt gtttctctat    1620
ttctctgttc cctgttgacc tcaagaaaaa aaaaaaaaaa aaaaaaaaaa aaaaaaaaaa    1680
aaaa                                                                1684

<210> SEQ ID NO 4
<211> LENGTH: 1404
<212> TYPE: DNA
<213> ORGANISM: Leishmania amazonensis

<400> SEQUENCE: 4
tcggcgtgtg gatgggcgat gtggattata ccggcacgct gccggagatg cctgcgagcg      60
tcgactacaa ggacgtcatg atcacggaac tgaacttcgg cgcaatgggc cagggactga    120 gcggacgct gccccctca tggagctcga tgaagcagct gatcgatctg gatctggagg       180
gcactaaggt gtccggcacg ctgccgcccg agtggagtgg gatggcgaag gccgaggccc    240
tgcagctgaa gtactgcgat ctgtccggga gtctgccccc ctcgtggtct tcgatgcaga    300
agctgcgtat cgtctcactg agcggcaacc acttctgcgg gtgcgtgccc gactcgtgga    360
```

```
gggagaagga ccgcctcgat gtgaccatcg aggaatggca catgggcgag gactgcaagc      420
ttgctaacgc ctgccgcccg actgctgctc cgggaacgac cacgactaac ccgcccacca      480
ccaccggcac cccagcagcc tcctctactc cttctccagg gtcggggtgc gaggtggatg      540
ggtgtgaggt gtgcgagggg gactccgctg cgcggtgcgc caggtgccgt gagggctact      600
ccctgacgga cgagaagacg tgcctggcga accacgatgg cggcgtggcg gcggcgtcaa      660
gcggagcggt ggctgcggct gctgtgtggg cggctgtgct gttgagcgtg gggctggtgg      720
cgtgagggtg cggcgggccc ctcttctctg tggtgcccct ggtgcctgcc ctcgccccg      780 gcacggcgtc gtcgctgccc tctctcaccc ccaccagccg acgggagac cgacagccac       840 acgcgcacgc gcacacgccg tcgtgcatcg cgtgtgcttt ccgccgttgt ggcgcctgca      900
cggatgcacg ggcatgcgga ggcgtgcatg cgtgtgcgcg tgccagctct tgtgtgtctc      960
tccgtgtggc cagcagtcgg cacccgcgcc gatcgaatgt gcgcgcggcg gcggtgtgtc     1020
gccttggaca gcgcgatgctg gcgcccgccc ctcgcgtgtg cctcggtctg cgtgtcgtgg     1080
ccgcgcgagc gacgtacgga gtgcgctgtg tgcacttaag gacatgtata tatgtatgtg     1140
tatgtatatg agtatgtata tatgtacggt tatatatagg aatttgtgta tgttgaggtg     1200
tatgcatgtg cgtgcgtata ttagtctgtg cgagcacgcg tgttgcgcca cgctttgctg     1260
cccgcctccg ctgtgggtgt cactcgctgt gggcccggtg gcgggtggcc ccgggtggtg     1320
cccgttcggc gggcggggc tcctctgtgt ttctctatttt ctctgttccc tgttgccctc     1380
caaaaaaaaa aaaaaaaaaa aaaa                                            1404

<210> SEQ ID NO 5
<211> LENGTH: 1501
<212> TYPE: DNA
<213> ORGANISM: Leishmania amazonensis

<400> SEQUENCE: 5
ccggcgtcgg cgtgtggatg ggcgatgtgg attataccgg cacgctgccg gagatgcctg       60
cgagcgtcga ctacaaggac gtcatgatca cggaactgaa cttcagcgca atgggccagg      120
ggctgagcgg gacgctgccc ccctcatgga gctcgctgac gtccttgata tcactgtgca      180
tcgaaaagtc tgagaaggtc accggcacgc tgcctgccca gtggagctcg atgacgtcgc      240
tggacaacct taacctgcac gacacggcgg tctccggcac gctgccgccc gagtggagtg      300
ggatgacgtc gctggacgac cttaacctgc acgacacggc ggtctccggc acgctgcctg      360
cccagtggag ctcgatgaag cagctgatcg atctggatct ggaggcact aaggtgtccg      420 gcacgctgcc gcccgagtgg agtgggatgg cgaaggccga ggccctgcag ctgaagtact      480
gcgatctgtc cgggagtctg ccccctcgt ggtcttcgat gcagaagctg cgtatcgtct       540
cactgagcgg caaccacttc tgcgggtgcg tgcccgactc gtggagggag aaggaccgcc      600
tcgatgtgac catcgaggaa tggcacatgg gcgaggacta caagcttgct aacgcctgcc      660
gcccgactgc tgctccggga acgaccacga ctaacccgcc caccaccacc ggcaccccag      720
cagcctcctc tactccttct ccagggtcgg ggtgcgaggt ggatgggtgt gaggtgtgcg      780
agggggactc cgctgcgcgg tgcgccaggt gccgtgaggg ctactccctg acggacgaga      840
agacgtgcct ggcgaaccac gatggcgcg tggcggcggc gtcaagcgga gcggtggctg      900
cggctgctgt gtgggcggct gtgctgttga gcgtggggct ggtggcgtga gggtgccgcc     960
gccccctctt ctctgtggtg ccctggtgc ctgcctcgc cccagcacg ggtcgtcgc        1020 tgccctctca cccccaccag ccgaagggga gaccgacagc cacacgcaca cgcgcacgcg     1080
```

-continued

```
ccgtcgtgca tcgcgtgtgc tttccgccgt tgtggcgcct gcgcggatgc acgggcatgc    1140
ggaggcgtgc atgcgtgtgc gcgtgccaac tcttgtgtgt ctctccgtgt ggccagcagt    1200
cggcacccgt gcacgtaagg acatgtatat atgtatgtgt aggtatatga gtatgtatat    1260
atgtacggtt atatatagga atttgtgtat gttgaggtat atgcatgtgc gtgcgtatat    1320
tagtctgtgc gagcacgcgt gttgcgccac gctctgctgc ccgcctctgc tgtgcgtgtc    1380
actcgctgtg ggcgcgctgg cgggtggcgc cgggtggtgg ccgtgcggcg ggcggggggct    1440 cctctgtgtt tctctatttc tctgttccct gttgacctca agaaaaaaaa aaaaaaaaaa    1500
a                                                                    1501
```

<210> SEQ ID NO 6
<211> LENGTH: 371
<212> TYPE: PRT
<213> ORGANISM: Leishmania amazonensis

<400> SEQUENCE: 6

```
Met Ala Gln Cys Val Arg Arg Leu Val Leu Ala Ala Pro Leu Ala Ala
1               5                  10                  15

Val Val Ala Leu Leu Leu Cys Thr Ser Ser Ala Pro Val Ala Arg Ala
            20                  25                  30

Ala Gly Thr Ser Asp Phe Thr Glu Ala Gln Gln Thr Asn Thr Leu Thr
        35                  40                  45

Val Leu Gln Ala Phe Ala Arg Ala Ile Pro Ala Leu Gly Asp Thr Trp
    50                  55                  60

Thr Gly Ser Asp Phe Cys Ser Trp Lys His Ile Ile Cys Asp Ser Pro
65                  70                  75                  80

Gly Val Gly Val Trp Met Gly Asp Val Asp Tyr Thr Gly Thr Leu Pro
                85                  90                  95

Glu Met Pro Ala Ser Val Asp Tyr Lys Asp Val Met Ile Thr Glu Leu
            100                 105                 110

Asn Phe Ser Ala Met Gly Gln Gly Leu Ser Gly Thr Leu Pro Pro Ser
        115                 120                 125

Trp Ser Ser Leu Thr Ser Leu Ile Ser Leu Cys Ile Glu Lys Ser Glu
    130                 135                 140

Lys Val Thr Gly Thr Leu Pro Ala Gln Trp Ser Ser Met Thr Ser Leu
145                 150                 155                 160

Asp Asn Leu Asn Leu His Asp Thr Ala Val Ser Gly Thr Leu Pro Ala
                165                 170                 175

Gln Trp Ser Ser Met Lys Gln Leu Thr Val Leu Asp Leu Glu Gly Thr
            180                 185                 190

Lys Val Ser Gly Thr Leu Pro Ser Glu Trp Ser Gly Met Ala Lys Ala
        195                 200                 205

Glu Ala Val Gln Leu Glu Asn Cys Gly Leu Ser Gly Ser Leu Pro Pro
    210                 215                 220

Ser Trp Ser Ala Met Pro Lys Leu Arg Ile Val Ser Leu Ser Gly Asn
225                 230                 235                 240

His Phe Cys Gly Cys Val Pro Asp Ser Trp Arg Glu Lys Asp Arg Leu
                245                 250                 255

Asp Val Thr Ile Glu Glu Trp His Met Gly Glu Asp Cys Lys Leu Ala
            260                 265                 270

Asn Ala Cys Arg Pro Thr Ala Ala Pro Gly Thr Thr Thr Asn Pro
        275                 280                 285

Pro Thr Thr Thr Gly Thr Pro Ala Ala Ser Ser Thr Pro Ser Pro Gly
    290                 295                 300
```

Ser Gly Cys Glu Val Asp Gly Cys Glu Val Cys Glu Gly Asp Ser Ala
305                 310                 315                 320

Ala Arg Cys Ala Arg Cys Arg Glu Gly Tyr Ser Leu Thr Asp Glu Lys
            325                 330                 335

Thr Cys Leu Ala Asn His Asp Gly Val Ala Ala Ser Ser Gly
            340                 345                 350

Ala Val Ala Ala Ala Val Trp Ala Ala Val Leu Leu Ser Val Gly
        355                 360                 365

Leu Val Ala
    370

<210> SEQ ID NO 7
<211> LENGTH: 286
<212> TYPE: PRT
<213> ORGANISM: Leishmania amazonensis

<400> SEQUENCE: 7

Met Gly Asp Val Asp Tyr Thr Gly Thr Leu Pro Glu Met Pro Ala Ser
1               5                   10                  15

Val Asp Tyr Lys Asp Val Met Ile Thr Glu Leu Asn Phe Ser Ala Met
            20                  25                  30

Gly Gln Gly Leu Ser Gly Thr Leu Pro Pro Ser Trp Ser Ser Leu Thr
        35                  40                  45

Ser Leu Ile Ser Leu Cys Ile Glu Lys Ser Glu Lys Val Thr Gly Thr
    50                  55                  60

Leu Pro Ala Gln Trp Ser Ser Met Thr Ser Leu Asp Asn Leu Asn Leu
65                  70                  75                  80

His Asp Thr Ala Val Ser Gly Thr Leu Pro Ala Gln Trp Ser Ser Met
                85                  90                  95

Lys Gln Leu Thr Val Leu Asp Leu Glu Gly Thr Lys Val Ser Gly Thr
            100                 105                 110

Leu Pro Ser Glu Trp Ser Gly Met Ala Lys Ala Glu Ala Val Gln Leu
        115                 120                 125

Glu Asn Cys Gly Leu Ser Gly Ser Leu Pro Pro Ser Trp Ser Ala Met
    130                 135                 140

Pro Lys Leu Arg Ile Val Ser Leu Ser Gly Asn His Phe Cys Gly Cys
145                 150                 155                 160

Val Pro Asp Ser Trp Arg Glu Lys Asp Arg Leu Asp Val Thr Ile Glu
                165                 170                 175

Glu Trp His Met Gly Glu Asp Cys Lys Leu Ala Asn Ala Cys Arg Pro
            180                 185                 190

Thr Ala Ala Pro Gly Thr Thr Thr Thr Asn Pro Pro Thr Thr Thr Gly
        195                 200                 205

Thr Pro Ala Ala Ser Ser Thr Pro Ser Pro Gly Ser Gly Cys Glu Val
    210                 215                 220

Asp Gly Cys Glu Val Cys Glu Gly Asp Ser Ala Ala Arg Cys Ala Arg
225                 230                 235                 240

Cys Arg Glu Gly Tyr Ser Leu Thr Asp Glu Lys Thr Cys Val Ala Asn
                245                 250                 255

His Asp Gly Gly Val Ala Ala Ser Ser Gly Ala Val Ala Ala Ala
            260                 265                 270

Ala Val Trp Ala Ala Val Leu Leu Ser Val Gly Leu Val Ala
        275                 280                 285

<210> SEQ ID NO 8

```
<211> LENGTH: 310
<212> TYPE: PRT
<213> ORGANISM: Leishmania amazonensis

<400> SEQUENCE: 8
```

| |

Arg Val Ala Pro Gly Ala Arg Ser Ala Gly Gly Ser Ser Val
    35                  40                  45

Phe Leu Tyr Phe Ser Val Pro Cys Cys Pro Lys Lys Lys Lys
50                  55                  60

Lys Lys Ile Gly Val Trp Met Gly Asp Val Asp Tyr Thr Gly Thr Leu
65                  70                  75                  80

Pro Glu Met Pro Ala Ser Val Asp Tyr Lys Asp Val Met Ile Thr Glu
                85                  90                  95

Leu Asn Phe Gly Ala Met Gly Gln Gly Leu Ser Gly Thr Leu Pro Pro
            100                 105                 110

Ser Trp Ser Ser Met Lys Gln Leu Ile Asp Leu Asp Leu Glu Gly Thr
        115                 120                 125

Lys Val Ser Gly Thr Leu Pro Pro Glu Trp Ser Gly Met Ala Lys Ala
    130                 135                 140

Glu Ala Leu Gln Leu Lys Tyr Cys Asp Leu Ser Gly Ser Leu Pro Pro
145                 150                 155                 160

Ser Trp Ser Ser Met Gln Lys Leu Arg Ile Val Ser Leu Ser Gly Asn
                165                 170                 175

His Phe Cys Gly Cys Val Pro Asp Ser Trp Arg Glu Lys Asp Arg Leu
            180                 185                 190

Asp Val Thr Ile Glu Glu Trp His Met Gly Glu Asp Cys Lys Leu Ala
        195                 200                 205

Asn Ala Cys Arg Pro Thr Ala Ala Pro Gly Thr Thr Thr Asn Pro
    210                 215                 220

Pro Thr Thr Thr Gly Thr Pro Ala Ala Ser Ser Thr Pro Ser Pro Gly
225                 230                 235                 240

Ser Gly Cys Glu Val Asp Gly Cys Glu Val Cys Glu Gly Asp Ser Ala
                245                 250                 255

Ala Arg Cys Ala Arg Cys Arg Glu Gly Tyr Ser Leu Thr Asp Glu Lys
            260                 265                 270

Thr Cys Leu Ala Asn His Asp Gly Gly Val Ala Ala Ser Ser Gly
        275                 280                 285

Ala Val Ala Ala Ala Val Trp Ala Ala Val Leu Leu Ser Val Gly
    290                 295                 300

Leu Val Ala
305

<210> SEQ ID NO 10
<211> LENGTH: 310
<212> TYPE: PRT
<213> ORGANISM: Leishmania amazonensis

<400> SEQUENCE: 10

Met Gly Asp Val Asp Tyr Thr Gly Thr Leu Pro Glu Met Pro Ala Ser
1               5                   10                  15

Val Asp Tyr Lys Asp Val Met Ile Thr Glu Leu Asn Phe Ser Ala Met
            20                  25                  30

Gly Gln Gly Leu Ser Gly Thr Leu Pro Pro Ser Trp Ser Ser Leu Thr
        35                  40                  45

Ser Leu Ile Ser Leu Cys Ile Glu Lys Ser Glu Lys Val Thr Gly Thr
    50                  55                  60

Leu Pro Ala Gln Trp Ser Ser Met Thr Ser Leu Asp Asn Leu Asn Leu
65                  70                  75                  80

His Asp Thr Ala Val Ser Gly Thr Leu Pro Pro Glu Trp Ser Gly Met
                85                  90                  95

```
Thr Ser Leu Asp Asp Leu Asn Leu His Asp Thr Ala Val Ser Gly Thr
            100                 105                 110

Leu Pro Ala Gln Trp Ser Ser Met Lys Gln Leu Ile Asp Leu Asp Leu
        115                 120                 125

Glu Gly Thr Lys Val Ser Gly Thr Leu Pro Pro Glu Trp Ser Gly Met
    130                 135                 140

Ala Lys Ala Glu Ala Leu Gln Leu Lys Tyr Cys Asp Leu Ser Gly Ser
145                 150                 155                 160

Leu Pro Pro Ser Trp Ser Ser Met Gln Lys Leu Arg Ile Val Ser Leu
                165                 170                 175

Ser Gly Asn His Phe Cys Gly Cys Val Pro Asp Ser Trp Arg Glu Lys
            180                 185                 190

Asp Arg Leu Asp Val Thr Ile Glu Glu Trp His Met Gly Glu Asp Cys
        195                 200                 205

Lys Leu Ala Asn Ala Cys Arg Pro Thr Ala Ala Pro Gly Thr Thr Thr
    210                 215                 220

Thr Asn Pro Pro Thr Thr Thr Gly Thr Pro Ala Ala Ser Ser Thr Pro
225                 230                 235                 240

Ser Pro Gly Ser Gly Cys Glu Val Asp Gly Cys Glu Val Cys Glu Gly
                245                 250                 255

Asp Ser Ala Ala Arg Cys Ala Arg Cys Arg Glu Gly Tyr Ser Leu Thr
            260                 265                 270

Asp Glu Lys Thr Cys Leu Ala Asn His Asp Gly Val Ala Ala Ala
        275                 280                 285

Ser Ser Gly Ala Val Ala Ala Ala Val Trp Ala Ala Val Leu Leu
    290                 295                 300

Ser Val Gly Leu Val Ala
305                 310

<210> SEQ ID NO 11
<211> LENGTH: 3088
<212> TYPE: DNA
<213> ORGANISM: Leishmania amazonensis

<400> SEQUENCE: 11
gcgctgctgc cgctggcgct gttgtgtgtg tgctggggcc gcgccacgca cacgcacggt    60 agtgagggg agccgcagcg accgaccggg cggagcgggc gggcggaggg gggcgctccc   120
gcccgctggt catgctctct gtttcgctgg ccggcctctc tacgccgctg cgtgggcgg   180 agctccgcgc tgcgtatcgc tcgccccctcg ctgcccctcc ctgcccctcc tcatgtgcac   240
tgctccctcc ctctcccctcc ctctacactc ctcgctgtcc cctcggccga cctccacgga   300
cacgcagacg tgcgtgcgca tacacaccac ccctcacctc gctgctgctg ctgtgacagc   360
tctacggacc ctgcccagtc gctgcgcccc cgccacccgc tctgtcccc cgcacgaggg   420 tacctacgac gtgccggcca cccgctctg cccgataagc tgagctggcg ctcacgcccg   480
agcaatcccc tcacggatct gctgccgcgc cgcactgctc ttgaccctgg ctgcgaatgg   540
cgctgtgcgt gcgtcggctg gtgctggcgg cgaccctcgc cgctgtggtg gcgctgctgc   600
tgtgcacgag cagtgcgccg gtggcgcgtg ctgctgtgaa ggatgacttc actgctgcgc   660
agcggacgaa cacgctggcg gtgctggagg cgtttgggcg tgcgatccct gagcttggga   720
agctgtggaa gggcgacgac ttctgctttt gggagtcggt cgtgtgcgat gtgaccgaag   780
tgtacttgtg ggaaatcggt gcgacgtata ccggcacgct gccggagatg cctgtggacg   840
tcgactacac ggccgtcatg gtcaagcacc tcgacttttc ccaaatgggg ctggggctga   900
```

```
gcggaacgct gccggacagc tggagcaggc tgcagggact gacctcactt acgttgtcgg    960
gctgcggcgt gagcggtacg ctgccccct cgtggcgctc gatgaagtct ttggtgtcgt   1020
tgtggattga gagttgtgaa agtgttaccg gcaagctgcc gcctgagtgg agctcgatga   1080
aatcgctgag agatctccat ctgcatggcg cgaaggtttc cggcacgctg ccgcctgagt   1140
ggagcacgat gaaatcgctg acccttctcg atctgcagga cactcaggtt accggcagtc   1200
tgccgcctga gtggagctca atgaaatcca tgaccattct cagtctgaat ggcgcgaagg   1260
tttccggcac gctgccaccc cagtggagct cgatgacatc gctgagcctt ctcagtctgg   1320
agggtactca gctctccggc acgctaccgc cccagtggag tgggatgaca tcgctggtca   1380
cgcttttct gcagggtact caggtctccg gcactctgcc gccgcagtgg agatcgatgt   1440
tgaatgccga gttcctgcag ctggagaact gcgacctgtc cggctgtttg ccccccgagt   1500
gggctgcgat gccgaagctg cgtcatgtcg aacttaaggg caaccagttc gccgggtgtg   1560
tgccggactc gtgggctcag aaggccggtc tcgttgtgga aatcgaggat aagcacacgg   1620
gcaacagctg cattgctggt gcggactgcg caacgacgac cacgaccacc actgaaccca   1680
cgtccactgc gagcccaaca gccacgccta cctctgcccc cgagacggag tgcgaggtgg   1740
atgggtgtga ggtgtgcgat ggggactccg cggcgaggtg cgccaggtgc cgtgagggct   1800
acttcctgac ggacgagagg acgtgcctgg tgtaccgcga tggcggcgtt gtggccgtgt   1860
cgatcggagc ggctgctgcc gctgttgtgt gcatggctgt gctgctgagc gtggggctgg   1920
cggcgtgagg atgccgctgc tgtcgcgcgc aggcggcggc accgctgcg tggcacacga   1980
ctgcgtgctt gcgtgcagca ccgcgccctg cattggcgtg cgtgtgcgcg tctgtgtgtg   2040
catggctgct gacggtgcct ttcgtcctgc ctctcgctgc ctctgcctct ctccgcgtgt   2100
gaatgctgtg ggctgtgttt ggggctctcg tgcggcgctg ctgtacggct gctgcttctt   2160
ctccacccct ctctctcgca tgccggcgag ggaggggtgg cacgtgcgcg tgtgccgctg   2220
cgcttgcgag tgcgtctgtg tgtgggcctt caccacgtgc tacggtcacg ccttctcggc   2280
tggccactcg cggcgctgag ggcggtgtgc ccttcccctc gagcgccgtc gcactctctt   2340
ccgcgcgcct gcgcgggctt cttcgtgcgc tgtgctcagc cgtgcgctct cacctctttc   2400
cctttcatt cgcttgtctt ctctcttctc ccccgcact gcggtctccc ctcctctgcc   2460
gtgcggtgcg caggcgggtg acttgccgtt gcgtctcccc ctttcgtgga gcgctgagcc   2520
gatccccctt cggcctcct cctccctcct cccgtgggtc ctgtctgttg tacatcgtcg   2580
gaccgtctct tcgtgttgcc tctccgcacc ttccgcaaat ctgcgctcgc ctgtgccgcc   2640
tctcggactt tatccttact gtgattgtat tctcacggtg cgtctccgtg tgtgtgtgtg   2700
ccacgcaccg cttcttccat gtgtgtcctt gcttgctctc gtctgccccc ccccctctgc   2760
ctcacacatt ccgtgcgtgt gtgcatcacc gttgggcggc gacatcggtg cccgtccctg   2820
ccaccctcta ctccctcatt ctcttgccac ttcgtgggcg gtgcgtgcat gcatggatgt   2880
atatacacgc atagaggggt ggggacgcgg gggatcctct agagtcgacc tgcaggcatg   2940
caagcttggc gtaatcatgg tcatagctgt ttcctgtgtg aaattgttat ccgctcacaa   3000
ttccacacaa catacgagcc ggaagcataa agtgtaaagc ctggggtgcc taatgagtga   3060
gctaactcac attaattgcg ttgcgctc                                    3088
```

<210> SEQ ID NO 12
<211> LENGTH: 464
<212> TYPE: PRT
<213> ORGANISM: Leishmania amazonensis

<400> SEQUENCE: 12

```
Met Ala Leu Cys Val Arg Arg Leu Val Leu Ala Thr Leu Ala Ala
1               5                   10                  15

Val Val Ala Leu Leu Cys Thr Ser Ser Ala Pro Val Ala Arg Ala
            20                  25                  30

Ala Val Lys Asp Asp Phe Thr Ala Ala Gln Arg Thr Asn Thr Leu Ala
        35                  40                  45

Val Leu Glu Ala Phe Gly Arg Ala Ile Pro Glu Leu Gly Lys Leu Trp
    50                  55                  60

Lys Gly Asp Asp Phe Cys Phe Trp Glu Ser Val Val Arg Cys Asp
65                  70                  75                  80

Arg Ser Val Leu Gly Gly Lys Ser Val Arg Arg Ile Pro Ala Arg Cys
                85                  90                  95

Arg Arg Cys Leu Trp Thr Ser Thr Thr Arg Pro Ser Trp Ser Ser Thr
            100                 105                 110

Ser Thr Phe Pro Lys Trp Gly Trp Gly Trp Ala Glu Arg Cys Arg Thr
        115                 120                 125

Ala Gly Ala Gly Cys Arg Asp Trp Pro His Leu Arg Cys Arg Ala Ala
    130                 135                 140

Ala Trp Ala Val Arg Cys Pro Pro Arg Gly Ala Arg Trp Ser Leu Trp
145                 150                 155                 160

Cys Arg Cys Gly Leu Arg Val Val Lys Val Leu Pro Ala Ser Cys Arg
                165                 170                 175

Leu Ser Gly Ala Arg Trp Asn Arg Trp Glu Ile Ser Ile Cys Met Ala
            180                 185                 190

Arg Arg Phe Pro Ala Arg Cys Arg Leu Ser Gly Ala Arg Trp Asn Arg
        195                 200                 205

Trp Pro Phe Ser Ile Cys Arg Thr Leu Arg Leu Pro Ala Val Cys Arg
    210                 215                 220

Leu Ser Gly Ala Gln Trp Asn Pro Trp Pro Phe Ser Val Trp Met Ala
225                 230                 235                 240

Arg Arg Phe Pro Ala Arg Cys His Pro Ser Gly Ala Arg Trp His Arg
                245                 250                 255

Trp Ala Phe Ser Val Trp Arg Val Leu Ser Ser Pro Ala Arg Tyr Arg
            260                 265                 270

Pro Ser Gly Ser Gly Met Thr Ser Leu Val Thr Leu Phe Leu Gln Gly
        275                 280                 285

Thr Gln Val Ser Gly Thr Leu Pro Pro Gln Trp Arg Ser Met Leu Asn
    290                 295                 300

Ala Glu Phe Leu Gln Leu Glu Asn Cys Asp Leu Ser Gly Cys Leu Pro
305                 310                 315                 320

Pro Glu Trp Ala Ala Met Pro Lys Leu Arg His Val Glu Leu Lys Gly
                325                 330                 335

Asn Gln Phe Ala Gly Cys Val Pro Asp Ser Trp Ala Gln Lys Ala Gly
            340                 345                 350

Leu Val Val Glu Ile Glu Asp Lys His Thr Gly Asn Ser Cys Ile Ala
        355                 360                 365

Gly Ala Asp Cys Ala Thr Thr Thr Thr Thr Thr Glu Pro Thr Ser
    370                 375                 380

Thr Ala Ser Pro Thr Ala Thr Pro Thr Ser Ala Pro Glu Thr Glu Cys
385                 390                 395                 400

Glu Val Asp Gly Cys Glu Val Cys Asp Gly Asp Ser Ala Ala Arg Cys
                405                 410                 415
```

-continued

```
Ala Arg Cys Arg Glu Gly Tyr Phe Leu Thr Asp Glu Arg Thr Cys Leu
            420                 425                 430

Val Tyr Arg Asp Gly Gly Val Val Ala Val Ser Ile Gly Ala Ala Ala
            435                 440                 445

Ala Ala Val Val Cys Met Ala Val Leu Leu Ser Val Gly Leu Ala Ala
        450                 455                 460
```

AGENTS FOR THE PREVENTION OF LEISHMANIASIS

This application is the U.S. national phase of international application PCT/FR2004/002955 filed 19 Nov. 2004, which designated the U.S. and claims priority to FR 0313555 filed 19 Nov. 2003, and FR 0407010 filed 25 Jun. 2004, the entire content of each of which is hereby incorporated by reference.

The invention relates to novel agents for the prevention of leishmaniasis in animals and in humans.

It relates in particular to nucleic acid molecules encoding virulence or pathogenicity factors in *Leishmania* and to the use thereof for producing such factors in order to develop vaccine compositions against leishmaniasis.

Leishmaniasis represents one of the six major parasitic diseases and is considered, in this respect, to be a priority by the World Health Organization (WHO). *Leishmania* exists in the extracellular promastigote form, inside the digestive tube of the vector insect (the sandfly), and in the intracellular amastigote form, in the mammalian host. Several molecules, including lypophosphoglycans (LPGs) or a metallo-protease called gp63, appear to play an important role in the infectious capacity and the the pathogenicity of the parasite. More recently, a family of glycoproteins, called promastigote surface antigens (PSAs), has raised new interest. These PSAs are characterized by the presence of leucine-rich repeats that can be involved in protein/protein interactions and confer Th 1-type cell-mediated protective immunity in mice. In organisms, such as bacteria or plants, it appears that PSAs were involved in functions such as cell adhesion, resistance to pathogens and signal transduction.

However, no biological role has been described or suggested in *Leishmania*.

It has been possible for this role to be studied by the inventors by means of the technique in their possession for culturing *Leishmania* promastigotes and amastigotes under serum-free and axenic conditions, with a completely defined medium, i.e. in which the constituents are all defined, and which is the subject of patent FR 93 05 779 of May 13, 1993, in the name of IRD (ex ORSTOM). The mastering of this method allows them to have parasitic forms free of the contaminants introduced up until now by the culture media, and antigenic determinants in a highly purified form.

In said applicant's FR patent, the isolation and the identification of an excreted/secreted PSA (excretion/secretion antigen, abbreviated to ESA) of 38 kDa and of 45 kDa in the culture supernatant of *L. amazonensis* have already been described.

The inventors have presently isolated and cloned the cDNA encoding this protein and evaluated its role in the biology of the parasite by developing an additional transgenesis strategy. These studies have made it possible to demonstrate the involvement of this PSA as a virulence and/or pathogenicity factor and to develop constructs for overexpressing the *Leishmania* gene encoding this PSA, which makes it possible to develop agents for producing vaccine compositions against leishmaniasis.

The aim of the invention is therefore to provide nucleic acid sequences being capable of encoding PSAs of promastigote forms and of amastigote forms of *Leishmania*, constituting virulence and/or pathogenicity factors.

It is directed more particularly toward providing vectors for the overexpression of these PSAs, and also genetically modified parasites.

The invention is also directed toward the culture medium supernatants of the PSAs obtained, and also the isolated, purified PSAs, and the beneficial use of their properties for developing vaccine compositions against leishmaniasis.

The nucleic acid sequences of the invention correspond to isolated nucleic acids capable of encoding a PSA of promastigote forms or of amastigote forms of *Leishmania*, said nucleic acids corresponding to one of the sequences SEQ ID No 1, SEQ ID No 2, SEQ ID No 3, SEQ ID No 4, SEQ ID No 5 and SEQ ID No 11, and encoding PSAs having the sequences, respectively, SEQ ID No 6, SEQ ID No 7, SEQ ID No 8, SEQ ID No 9, SEQ ID No 10 and SEQ ID No 12.

The nucleic acid sequences of the invention are more especially sequences of cDNA clones belonging to a family corresponding to the characteristics illustrated by FIG. 2 and comprising in particular a SalI restriction site and two HindIII restriction sites, with a stop codon located downstream of the first HindIII site.

The invention is directed in particular toward the cDNA clones of said family comprising an EcoRV and/or PstI restriction site between the two sites SalI and HindIII, or on either side of the SalI site.

The invention is also directed toward the isolated immunogenic proteins, characterized in that they have a sequence as encoded by the nucleic acids defined above. It is directed in particular toward the proteins corresponding to the sequences SEQ ID No 6, SEQ ID No 7, SEQ ID No 8, SEQ ID No 9, SEQ ID No 10 or SEQ ID No 12.

Figure 3A:
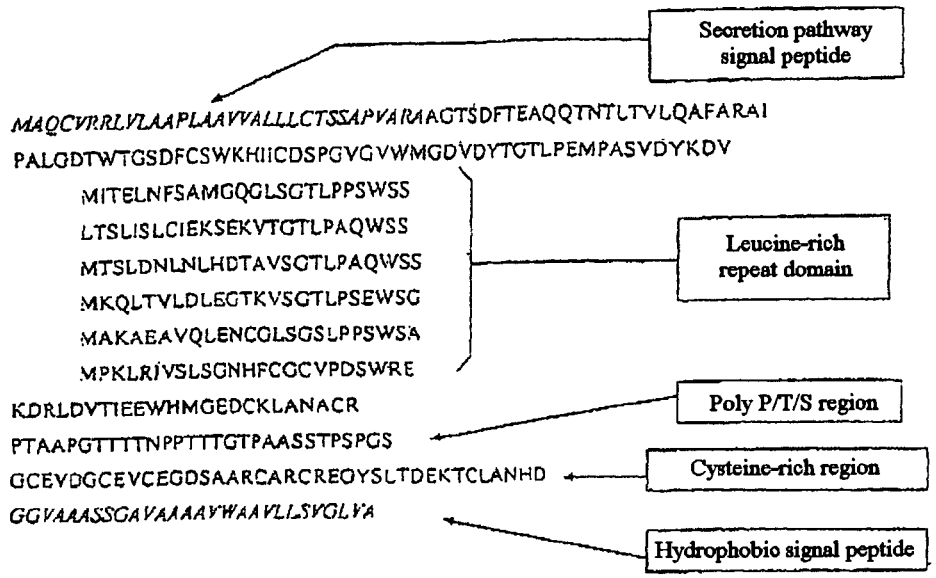
Figure 3B:
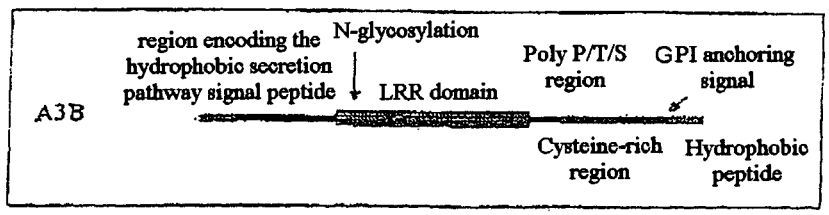

These proteins belong to the "promastigote surface antigen" (abbreviated to PSA) family and possess characteristic regions illustrated in FIGS. 3A and 3B. These proteins can be post-translationally modified by means of N-glycosylations, phosphorylations and anchoring of a GPI. They possess a hydrophobic signal peptide in the carboxy-terminal position.

The inventors have obtained constructs that make it possible to express the sequences defined above, in the sense position, in an expression vector, by directional cloning of said sequences.

The invention is therefore directed toward nucleic acid constructs, characterized in that they comprise isolated nucleic acids in the sense position, capable of encoding an immunogenic protein of promastigote forms or of amastigote forms of *Leishmania*, these proteins corresponding to one of the sequences SEQ ID No 6, SEQ ID No 7, SEQ ID No 8, SEQ ID No 9, SEQ ID No 10 and SEQ ID No 12.

The invention is directed in particular toward the nucleic acid constructs comprising sequences of cDNA clones belonging to a family corresponding to the characteristics illustrated in FIG. 2 and comprising in particular a SalI restriction site and two HindIII restriction sites, with a stop codon located downstream of the first HindIII site.

The cDNA clones comprising an EcoRV and/or PstI restriction site between the two sites SalI and HindIII, or on either side of the SalI site, are particularly preferred.

Particularly advantageous constructs comprise, as nucleic acid sequences, a sequence chosen from SEQ ID No 1, SEQ ID No 2, SEQ ID No 3, SEQ ID No 4, SEQ ID No 5 and SEQ ID No 11, these sequences encoding, respectively, proteins having the sequences SEQ ID No 6, SEQ ID No 7, SEQ ID No 8, SEQ ID No 9, SEQ ID No 10 and SEQ ID No 12.

Preferred constructs comprise said nucleic acid sequences in a rapid multiplication plasmid such as pTex.

The invention is also directed toward the *Leishmania* strains transfected with such constructs, whether promastigote forms or amastigote forms are involved.

Transfected strains that are preferred, taking into account the vaccine applications targeted, are *L. infantum* strains.

Advantageously, the PSAs are produced in large amount, constitutively, in the parasites.

The invention is also directed toward a method of transfecting a *Leishmania* parasite, characterized in that a vector as defined above, comprising a marker, is introduced into the *Leishmania* parasite, the transfected parasites are selected by means of said marker, they are placed in culture in a completely defined axenic and serum-free medium, and the culture supernatant which contains the immunogenic proteins present in concentrations of the order of 10 to 20 times higher than that produced by the *Leishmania* mother strain is recovered.

The introduction of the vector into the parasite is, for example, carried out by electroporation.

The insertion of these nucleic acids into the parasites makes it possible to increase the infectious capacity of the latter: their ability to survive in the infected macrophage and to multiply therein is up to 5 times greater than that of the parasite not transfected with such nucleic acids.

Said PSAs are produced in large amount in the parasite culture medium supernatant. The invention is therefore also directed toward the culture medium supernatants of said genetically modified parasites, and also the PSAs isolated from these supernatants and purified.

The invention thus provides agents of great value for satisfying the industrial demand for large amounts of proteins constituting virulence/pathogenicity factors in *Leishmania*.

Due to their immunogenic capacity, these proteins make it possible to obtain, after immunization of animals according to conventional techniques, polyclonal antibodies and to develop monoclonal antibodies. The immunization of mice has thus made it possible to obtain anti IgG2A antibodies and that of dogs has made it possible to obtain IgG2 antibodies.

The invention is therefore also directed toward such antibodies and makes beneficial use of their properties for developing, on an industrial exportable scale, vaccine compositions against *leishmania* in humans or animals.

The diagnostic applications of these antibodies are also part of the invention.

Figure 4:
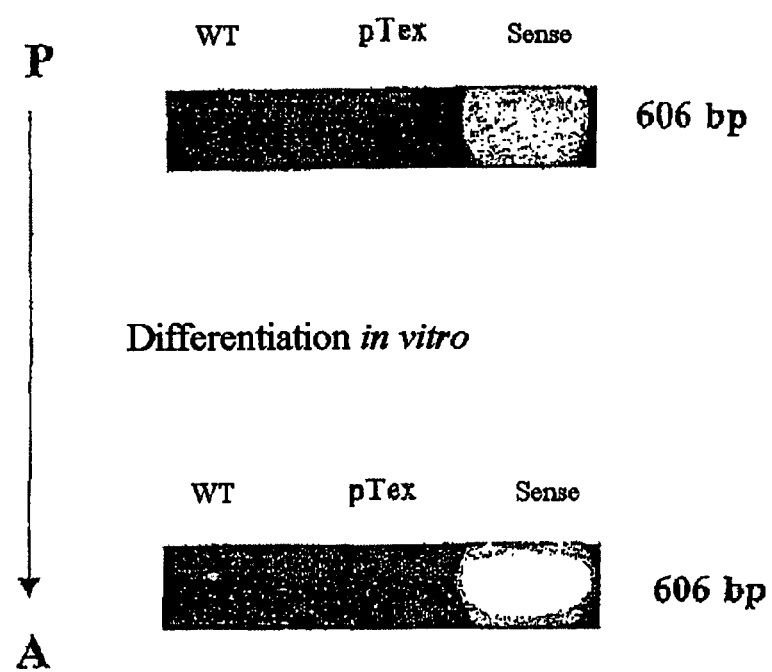
Figure 8:
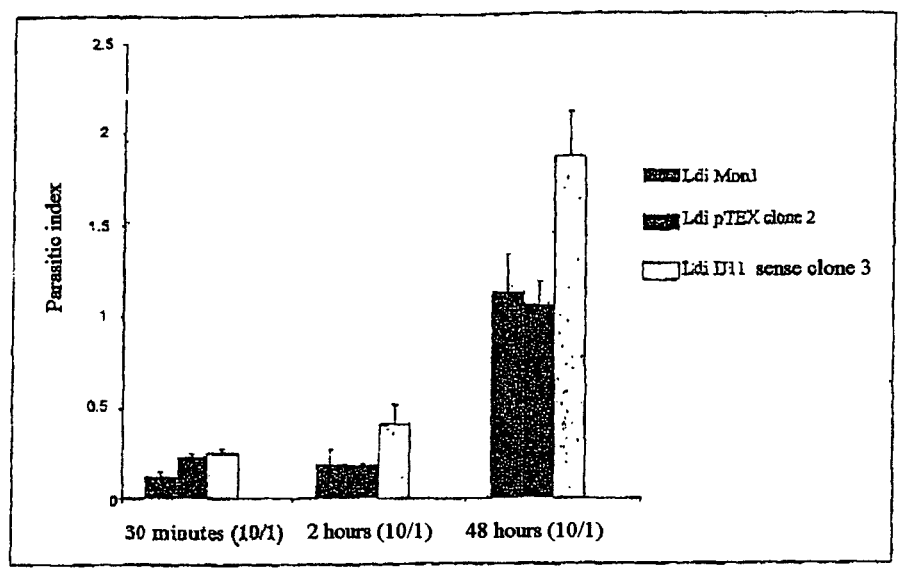

Other characteristics and advantages of the invention will be given in the examples which follow, in which reference will be made to FIGS. 1 to 8, which represent, respectively:

FIG. 1, the 3' alignment of the nucleotide sequences of cDNA clones according to the invention;

FIG. 2, a recapitulative diagram of the nucleotide sequences of the cDNA clones obtained after immunoscreening, with an anti-ESA monoclonal antibody, of *L. amazonensis* promastigote form and amastigote form expression libraries. The restriction enzyme sites are indicated above each sequence;

FIG. 3A, the location of various protein regions, characterized by their specific amino acid composition, present on the protein sequence deduced from the cDNA of the clone A3B; and FIG. 3B, a diagrammatic representation of the protein sequence deduced from the cDNA of the clone A3B encoding a PSA;

FIG. 4, the analyses of the transcripts by RT-PCR in the promastigote (P) and amastigote (A) forms;

FIG. 5, the level of production of the protein by Western blotting, using an anti-PSA antibody;

FIG. 6, the effect of the overexpression of a PSA of *L. amazonensis* on the infectious capacity of the parasites;

FIG. 7, the nucleotide sequences SEQ ID Nos 1 to 5 and 11, respectively, of the clones A3B, 2C1, 1A1, 2G1 and W2 of *L. amazonensis* promastigotes and amastigotes and IJ11 of *L. infantum* promastigotes, and the corresponding encoded amino acid sequences SEQ ID Nos 6 to 10 and 12, and FIG. 8, the parasitic index determined during the in vitro infection of canine macrophages with a wild-type strain or selected *L. infantum* promastigote clones, at various incubation times.

1-MOLECULAR CHARACTERIZATION OF THE MAJOR IMMUNOGENS OF THE ESAs OF PROMASTIGOTE AND AMASTIGOTE FORMS OF *L. amazonensis* (ABBREVIATED TO Lma)

This characterization was carried out by screening *L. amazonensis* promastigote form and amastigote form cDNA expression libraries using a monoclonal antibody directed against the ESA major immunogen.

cDNA Library Characteristics:

Two cDNA expression libraries, respectively of promastigote forms and of amastigote forms of *L. amazonensis*, were produced. The characteristics of these libraries are given in table I. The exponential-phase and stationary-phase parasites were mixed in order to have access to the various transcripts that may be expressed during the various stages of the in vitro culturing thereof. $5 \times 10^4$ phages per library were then immunoscreened with the monoclonal antibody F5 diluted to 1/500. The production of this antibody is the subject of the example in the FR patent mentioned above.

TABLE I

| cDNA library Lma LES D4 + D7 | Promastigotes | Amastigotes |
|---|---|---|
| Harvest D4 + D7 | $7.8 \cdot 10^9$ | $7.8 \cdot 10^9$ |
| Titration after packaging | 350 000 | 500 000 |
| Titer after amplification | $8.32 \cdot 10^7$ pH/ul | $2.16 \cdot 10^8$ pH/ul |

D4 + D7 = parasites harvested on the 4th day, in the exponential phase, and on the 7th day, in the stationary phase of their growth.

Isolation and Sequencing of the Clones Recognized by the Monoclonal Antibody F5

13 clones of the promastigote library were found to be positive and 11 clones of the amastigote library were found to be positive. All these clones were isolated by secondary and tertiary screening.

The plasmid DNA of all the clones isolated was analyzed after various enzymatic digestions and the cDNAs having larger inserts, by EcoRI/XhoI digestion, were selected in order to eliminate the cDNAs that were too truncated in the 5' position. As shown in table II, the clones 1A1, 1B1, 2B3, 2C1, 2D1 and 2E1 of the promastigote cDNA library and the clones A3B, V4A, V5, W2 and W3 of the amastigote library exhibit the larger inserts.

The analysis of these clones, by determining the presence or absence of two previously selected restriction enzyme sites (HindIII and SalI), show that they exhibit strong homology of their nucleotide sequence.

Three different classes of clones were demonstrated, by double HindIII/SalI digestion, with a HindIII/SalI fragment less than 400 bp in size (clone 2G1), 500 bp in size (clones of type 2C1 and A3B) or 600 bp in size (clones of type 1A1 or W2), respectively. Thus, five types of clones, chosen according to the specific characteristics of their DNA (the size of the insert and the location of certain restriction enzyme sites) are represented in bold characters in table II.

TABLE II

| | Lma promastigote cDNA library | | | | | | | | | | | | |
|---|---|---|---|---|---|---|---|---|---|---|---|---|---|
| | cDNA clones | | | | | | | | | | | | |
| | 1A1 | 1B1 | 1C1 | 1D5 | 1F1 | 2A2 | 2B3 | 2C1 | 2D1 | 2E1 | 2F1 | 2G1 | B3A |
| Size of the EcoRI/XhoI inserts (kb) Restriction map | 2.5 | 2.5 | 2-2.2 | 0.5 | 2 | 2 (>) | 2.5 | 2.4 | 2.4 | 2.4 | 2 | 1.7-2 | 1.7 |
| SalI | Y | Y | Y | N | N | N | Y | Y | Y | Y | N | Y | N |
| HindIII | 1.1 | 1.1 | 1.1 | / | 1.1 | 1.1 | 1.1 | 1.1 | 1.1 | 1.1 | 1.1 | 1.1 | 1.1 |
| HindIII/SalI (bp) Recombinant protein expression | 600 | 600 | 500 | N | N | N | 600 | 500 | 500 | 500 | N | <400 | N |
| (kDa) | 45 | / | 40 | / | / | / | / | 42.5 | / | / | 39 | ? | 18 |

| | Lma amastigote cDNA library | | | | | | | | | | |
|---|---|---|---|---|---|---|---|---|---|---|---|
| | cDNA clones | | | | | | | | | | |
| | A3B | V1B | V2D | V3A | V4A | V5 | W1A | W1C | W2 | W3 | W5 |
| EcoRI/XhoI (kb) Restriction map | 2.3 | 2-2.2 | 2.2 | ? | 2.3 | 2.3 | 2 | 2 | 2.3 | 2.2 | 1.7 |
| SalI | Y | Y | Y | N | Y | Y | N | N | Y | Y | N |
| HindIII | 1.1 | 1.1 | 1.1 | 1.1 | 1.1 | 1.1 | 1.1 | 1.1 | 1.1 | 1.1 | 1.1 |
| HindIII/SalI (bp) Recombinant Protein expression | 505 | 500 | 500 | N | 500 | 500 | N | N | 600 | 500< | N |
| (kDa) | 42.5 | / | 36.5 | / | 36.5 | 43 | / | / | 45 | / | / |

Y = yes, for site present;
N = no, for site absent;
/ = performed;
? = result not obtained.

Table II also gives the results relating to the ability of the clones to express a recombinant protein. IPTG was used as an inducing agent. The samples were analyzed by SDS-PAGE and immunoblotting in the presence of the antibody against promastigote form and/or amastigote form ESA, preabsorbed in the presence of *E. coli* lysate. Equivalent results are obtained. For clones of interest, the expression of various recombinant proteins ranging from 42.5 kDa in apparent molecular weight (clone 2C1), to 43 kDa (clone A3B) or 45 kDa (1A1 and W2) is noted.

The "sequence listing" document reports the results of the sequencing:

of the following three types of clones of the promastigote library:

the clone of type 1A1 (SEQ ID No 3), which expresses a protein, of sequence SEQ ID No 8, of higher molecular weight. The clones of type 1B1 and 2B3 are of the same type as this clone;

the clone 2C1 (SEQ ID No 2), which expresses a recombinant protein of molecular weight lower than that of the clone 1A1, having a sequence SEQ ID No 7;

the clone 2G1 (SEQ ID No 4), which has the particularity of possessing a small HindIII/SalI fragment, which expresses a recombinant protein of molecular weight lower than that of the clone 1A1, having a sequence SEQ ID No 9;

of the following two clones of the amastigote library:

the clones of type A3B (SEQ ID No 1), which express a recombinant protein of approximately 43 kDa, of sequence SEQ ID No 6 and having a 500 bp HindIII/SalI fragment, the clone V5 appearing to be identical. The clones V2D and V4A are considered to be truncated clones of the same type;

the clone W2 (SEQ ID No 5), which expresses a recombinant protein of 45 kDa, of sequence SEQ ID No 10 and which has a 600 bp HindIII/SalI fragment.

Study of the Five cDNA Sequences

The alignment of the five cDNA sequences obtained is represented in FIG. 1, where the differences between these clones are only due to the presence of a 5'-truncated sequence and/or the insertion of sequences of approximately 72 nucleotides of the 5' side. The clones thus exhibit one (clones 2C1 and A3B) or three (clones 1A1 and W2) insertions. Outside these insertion zones, the clones exhibit homologies of the order of 99% and can be considered to belong to a cDNA family. Only the clone A3B has the ATG initiation codon, the other clones being 5'-truncated. However, the A3B cDNA does not have the 39 nt sequence encoding the "splice leader" found in the 5' position on all *Leishmania* mRNAs.

The cDNAs of the clones A3B and 2C1 exhibit virtually total homology and are therefore considered to be identical, the cDNA of the clone 2C1 corresponding to a 5'-truncated portion of the cDNA of the clone A3B.

The clone A3B, representative of this family, was the subject of complete sequencing in both directions.

The restriction enzyme sites for each of these clones are reported in FIG. 2.

The sequences SEQ ID Nos 1 to 5 correspond, respectively, to those of the cDNAs of A3B, 2C1, 1A1, 2G1 and W2.

Analysis of the Various Deduced Protein Sequences

The translation of the various cDNA sequences into protein sequences was carried out by choosing the reading frame corresponding to that suggested by the position of the initiation codon on the plasmid pB-SK, the transcription of which is under the control of the promoter of the lacZ gene subjected to induction with IPTG.

The A3B protein exhibits the regions illustrated in FIGS. 3A and 3B. At the $NH_2$-terminal, a hydrophobic peptide, which can be cleaved, and which is described in the literature as a secretion pathway signal peptide, is identified. This is followed by the leucine-rich repeat domain, the clone A3B possessing 6 repeats. About ten amino acids from the end of this domain is a region rich in proline, threonine and serine, hereinafter called poly P/T/S region. This region is followed by a cysteine-rich region, that can be involved in disulfide bridges. Finally, the protein sequence ends with a hydrophobic signal peptide.

The cDNAs of the clones A3B and 2C1 exhibit virtually total homology and are therefore considered to be identical, the cDNA of the clone 2C1 corresponding to a 5'-truncated portion of the cDNA of the clone A3B.

The clone A3B, representative of this family, was the subject of complete sequencing in both directions.

The restriction enzyme sites for each of these clones are reported in FIG. 2: Nt=nucleotides; ATG=initiation codon; TAG=stop codon.

Analysis on the PROSITE database shows that the A3B protein has an N-glycosylation site located at the end of each leucine-rich repeat domain, and 12 potential phosphorylation sites.

Analysis of the location of this protein on the PSORT server predicts a cytoplasmic location at 92%, which indicates that the protein is soluble. This protein is probably anchored to the surface via a glycosyl phosphatidyl inositol or GPI. The hydrophobic signal peptide can therefore be cleaved and allow anchoring of the GPI at the level of asparagine (D).

The theoretical molecular weight of the protein of the clone A3B differs by approximately 2.9 kDa from that of the 1A1 and W2 proteins, which is in agreement with the difference of 2.5 kDa observed between the corresponding recombinant proteins. This difference is due to the presence of a variable number of leucine-rich repeats or LRRs, each also exhibiting a specific amino acid composition.

The apparent and theoretical molecular weights of the four types of PSA of the invention are given in table III below.

TABLE III

| Type of PSA | MW of the recombinant protein | Theoretical MW (nontruncated) | MW without signal peptide (3.2 kDa) |
| --- | --- | --- | --- |
| 4 LRR (2G1) | / | 33.5 kDa | 30.3 kDa |
| 6 LRR (A3B) | 42.5 kDa | 38.5 kDa | 35.3 kDa |
| 7 LRR (1A1 and W2) | 45 kDa | 41.4 kDa | 38.2 kDa |

2-Obtaining Genetically Modified Parasites:

Directional cloning of the LaPSA 38s gene into the expression vector pTex made it possible to obtain a construct capable of expressing the PSA gene in the sense position. The plasmid pTex-LaPSA 38s sense orientation and the empty vector pTex were then electroporated into the wild-type strain *Leishmania infantum* Mon 1 Clone 1, and the parasites were then selected with geneticin.

The study was carried out on wild-type (WT) parasites of the species *L. infantum*, those transfected with empty pTex (pTex) and those transfected with pTex containing the nucleotide sequence of interest (sense).

Molecular Characterization:

The analysis of the total DNA by Southern blotting shows that the sense construct is stable and amplified in the transformed strain. The results are given in FIG. 4, which gives the analyses of the transcripts by RT-PCR in the two forms, promastigotes (P) and amastigotes (A). FIG. 5 gives the level of production of the protein by Western blotting, using an anti-PSA. antibody (FIG. 5A: constitutive proteins; FIG. 5B: excreted/secreted proteins).

Phenotypic Characterization of the Mutants:

The comparison of the growth kinetics between Ldi WT, Ldi pTex and Ldi Sense shows that the overexpression of LaPSA 38s does not interfere with the growth of the parasites. Only a longer lag phase is observed for the strains transformed with the wild-type strain.

The sensitivity to lysis by human complement was also studied. Recently, it was demonstrated that *L. amazonensis* PSA had the property of inhibiting the action of complement in vitro. The "sense" promastigotes are more sensitive to complement. The excess PSA at the surface of the parasites can thus lead to cleavage and also to a greater formation of complexes engendering increased lysis.

Study of Infectious Capacity of the Parasites

To study the effect of the overexpression of LaPSA 38s on the infectious capacity of the parasites, the first approach consisted in bringing promastigotes of the transformed strains into contact with macrophages from dog, which is the natural domestic reservoir for visceral leishmaniasis.

Figure 6A:
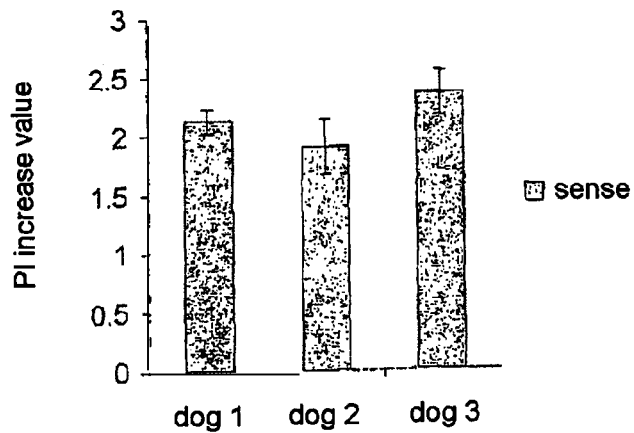
Figure 6B:
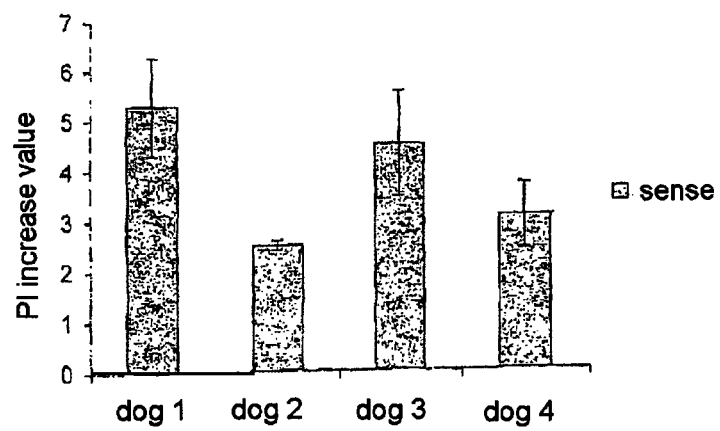

FIGS. 6A and 6B give the results obtained, respectively, 2 h after contact with the promastigotes and 48 h after contact with the amastigotes; in these figures, the parasitic index corresponds to the % of macrophages infected with the Sense strain×the number of parasites per macrophage/% of macrophages infected with the control strain (pTex)×the number of parasites per macrophage.

The promastigotes overexpressing LaPSA 38s exhibit twice as much infectious capacity with respect to canine macrophages. Furthermore, after phagocytosis, the amastigotes expressing the transgene possess a capacity to survive and to multiply in the parasitophorous vacuole that is significantly greater (2.5 to 5 times) than that of the control transfected with the empty vector.

2-Molecular Characterization of the *L. infantum* Promastigote ESAs

The nucleotide sequence of the *L. infantum* promastigote clone IJ11 is given in FIG. 7 (SEQ ID No 11) along with the corresponding amino acid sequence (SEQ ID No 12).

FIG. 8 reports the parasitic index determined during the in vitro infection of canine macrophages with the wild-type strain or the various selected *L. infantum* promastigote form clones (MHON/MA/67/ITMAP-263, clone 2), at various incubation times. The examination of these results shows attachment of the parasites to the macrophages after 30 min, penetration of the parasites after 2 hours and survival and multiplication of the intracellular amastigotes at 48 hours.

The invention claimed is:

1. An isolated immunogenic glycoprotein comprising SEQ ID NO:6, said glycoprotein being a *Leishmaniasis* surface antigen and an excreted/secreted antigen with an apparent molecular weight of 42.5 kDa.

2. An isolated immunogenic glycoprotein, the protein being encoded by a nucleic acid sequence comprising SEQ ID NO:1, said glycoprotein being a *Leishmaniasis* surface antigen and an excreted/secreted antigen with an apparent molecular weight of 42.5 kDa.

3. A method of immunization, said method comprising administration of the glycoprotein of claim 1 to an animal such that a specific immune response is elicited.

4. A method of immunization, said method comprising administration of the glycoprotein of claim 2 to an animal such that a specific immune response is elicited.

5. An isolated peptide comprising SEQ ID NO:6.

6. An isolated peptide encoded by a nucleic acid sequence comprising SEQ ID NO:1.

7. An isolated recombinant immunogenic glycoprotein comprising SEQ ID NO:6, said glycoprotein being a *Leishmaniasis* surface antigen and an excreted/secreted antigen with an apparent molecular weight of 42.5 kDa.

8. An isolated recombinant immunogenic glycoprotein, the protein being encoded by a nucleic acid sequence comprising SEQ ID NO:1, said glycoprotein being a *Leishmaniasis* surface antigen and an excreted/secreted antigen with an apparent molecular weight of 42.5 kDa.

9. An isolated recombinant peptide comprising SEQ ID NO:6.

10. An isolated recombinant peptide encoded by a nucleic acid sequence comprising SEQ ID NO:1.

* * * * *